US011241512B2

(12) United States Patent
Dave et al.

(10) Patent No.: US 11,241,512 B2
(45) Date of Patent: *Feb. 8, 2022

(54) STABILIZED RADIO-LABELED ANTI-CD45 IMMUNOGLOBULIN COMPOSITIONS

(71) Applicant: Actinium Pharmaceuticals, Inc., New York, NY (US)

(72) Inventors: Kaushik Dave, Edison, NJ (US); Shubh Sharma, Cranbury, NJ (US)

(73) Assignee: Actinium Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/456,614

(22) Filed: Jun. 28, 2019

(65) Prior Publication Data

US 2019/0321498 A1 Oct. 24, 2019

Related U.S. Application Data

(63) Continuation of application No. 15/603,817, filed on May 24, 2017, now Pat. No. 10,420,851, which is a continuation-in-part of application No. PCT/US2017/021076, filed on Mar. 7, 2017.

(60) Provisional application No. 62/304,537, filed on Mar. 7, 2016.

(51) Int. Cl.
| | |
|---|---|
| *A61K 51/10* | (2006.01) |
| *A61K 35/28* | (2015.01) |
| *C07K 16/28* | (2006.01) |
| *C07K 16/30* | (2006.01) |
| *A61K 39/395* | (2006.01) |
| *A61K 9/00* | (2006.01) |
| *A61K 47/22* | (2006.01) |
| *A61K 47/32* | (2006.01) |
| *A61K 47/42* | (2017.01) |
| *A61K 35/12* | (2015.01) |
| *A61K 39/00* | (2006.01) |

(52) U.S. Cl.
CPC ........ *A61K 51/1069* (2013.01); *A61K 9/0019* (2013.01); *A61K 35/28* (2013.01); *A61K 39/39591* (2013.01); *A61K 47/22* (2013.01); *A61K 47/32* (2013.01); *A61K 47/42* (2013.01); *A61K 51/1096* (2013.01); *C07K 16/289* (2013.01); *C07K 16/3061* (2013.01); *A61K 2035/124* (2013.01); *A61K 2039/505* (2013.01); *C07K 2317/51* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,102,990 | A | 4/1992 | Rhodes |
| 5,393,512 | A | 2/1995 | Vanderheyden |
| 5,961,955 | A | 10/1999 | Shochat |
| 10,420,851 | B2 * | 9/2019 | Dave ...................... A61K 35/28 |
| 2001/0055563 | A1 | 12/2001 | Zamora et al. |
| 2004/0115207 | A1 | 6/2004 | Irwin et al. |
| 2015/0216977 | A1 | 8/2015 | Adocia |

FOREIGN PATENT DOCUMENTS

| | | |
|---|---|---|
| CN | 101831434 A | 9/2010 |
| WO | 199855154 | 12/1998 |
| WO | 2009037190 | 3/2009 |
| WO | 2016187514 | 11/2016 |

OTHER PUBLICATIONS

Pagel et al., Comparison of Anti-CD20 and Anti-CD45 Antibodies for Conventional and Pretargeted Radioimmunotherapy of B-Cell Lymphomas, Blood, vol. 101, No. 6, p. 2340-2348, Mar. 15, 2003.
Gopal et al., Anti-CD45 radioin1Illunotherapy effectively targets and treats T-cell non-Hodgkin lymphoma, Blood, vol. 13, No. 23, p. 5905-5910, 2009.
Matthews, Dana C. et al., Clinical Observations, Interventions and Therapeutic Trials. Phase I Study of 1311-anti-CD45 antibody plus cyclophosphamide and total body irradiation for advanced acute leukemia and myelodysplastic syndrome, Blood, vol. 94, No. 4, p. 1237-1247, Aug. 15, 1999, American Society of Hematology.
Yale, Jen, Actinium Pharmaceuticals—Two Novel Acute Myeloid Leukemia (AML) Radiotherapeutics in Development Supported by Strong Balance Sheet, Laidlaw & Company, p. 1-20, Feb. 16, 2015.

* cited by examiner

*Primary Examiner* — Yunsoo Kim
(74) *Attorney, Agent, or Firm* — Dentons Cohen & Grigsby P.C.

(57) ABSTRACT

Compositions and methods are described for stabilizing a radio-iodinated monoclonal IgG antibody for up to 17 days against radiolytic decomposition. The stabilized radiolabeled murine antibody binding the CD45 antigen expressed on various forms of lymphomas is useful as a radio-therapeutic and diagnostic agent in the treatment of human malignancies of hematopoietic origin, including lymphomas.

8 Claims, 14 Drawing Sheets

Specification includes a Sequence Listing.

FIG. 1

| Variable Light Chain (VL) | DIALTQSPASLAVSLGQRATISCRASKSVSTSGYSYLHWYQQKPGQPPKLLIYLAS NLESGVPARFSGSGSGTDFTLNIHPVEEEDAATYYCQHSRELPFTFGSGTKLEIK<br><br>(Sequence ID No: 1) |
|---|---|
| Variable Heavy Chain (VH) | EVKLLESGGGLVQPGGSLKLSCAASGFDFSRYWMSWVRQAPGKGLEWIGEINPTSS TINFTPSLKDKVFISRDNAKNTLYLQMSKVRSEDTALYYCARGNYYRYGDAMDYWG QGTSVTVSSAK<br><br>(Sequence ID No: 2) |

FIG. 2

The Light Chain CDRs:
  LC-CDR-1:   RASKSVSTSGYSYLH        (Sequence ID NO:3)
  LC-CDR-2:   LASNLES                (Sequence ID NO:4)
  LC-CDR-3:   QHSRELPFT              (Sequence ID NO:5)

The Heavy Chain CDRs:
  HC-CDR-1:   GFDFSRYWMS             (Sequence ID NO:6)
  HC-CDR-2:   EINPTSSTINFTPSLKD      (Sequence ID NO:7)
  HC-CDR-3:   GNYYRYGDAMDY           (Sequence ID NO:8)

The Light Chain N-term:   DIALTQS        (Sequence ID NO:11)

The Heavy Chain N-term:   EVKLLES        (Sequence ID NO:12)

FIG. 3

|     |     | Leader Sequence |     |     |     |     |     |     |     |     |     |     |     |     |
|-----|-----|-----|-----|-----|-----|-----|-----|-----|-----|-----|-----|-----|-----|-----|
|     | M   | E   | T   | D   | T   | L   | L   | L   | W   | V   | L   | L   | L   | W   | V |
| 1   | ATG | GAG | ACA | GAC | ACA | CTC | CTG | TTA | TGG | GTA | CTG | CTG | CTC | TGG | GTT |

|     | Leader Sequence |     |     |     |     |     | FR1 |     |     |     |     |     |     |
|-----|-----|-----|-----|-----|-----|-----|-----|-----|-----|-----|-----|-----|-----|-----|
|     | P   | G   | S   | T   | G   | D   | I   | A   | L   | T   | Q   | S   | P   | A   | S |
| 46  | CCA | GGT | TCC | ACT | GGT | GAC | ATT | GCG | CTG | ACA | CAG | TCT | CCT | GCT | TCC |

|     |     |     |     |     |     | FR1 |     |     |     |     |     |     | CDR1 |     |
|-----|-----|-----|-----|-----|-----|-----|-----|-----|-----|-----|-----|-----|-----|-----|
|     | L   | A   | V   | S   | L   | G   | Q   | R   | A   | T   | I   | S   | C   | R   | A |
| 91  | TTA | GCT | GTA | TCT | CTG | GGA | CAG | AGG | GCC | ACC | ATC | TCA | TGC | AGG | GCC |

|     |     |     |     |     |     | CDR1 |     |     |     |     |     |     | FR2 |     |
|-----|-----|-----|-----|-----|-----|-----|-----|-----|-----|-----|-----|-----|-----|-----|
|     | S   | K   | S   | V   | S   | T   | S   | G   | Y   | S   | Y   | L   | H   | W   | Y |
| 136 | AGC | AAA | AGT | GTC | AGT | ACA | TCT | GGC | TAT | AGT | TAT | CTG | CAC | TGG | TAC |

|     |     |     |     |     |     | FR2 |     |     |     |     |     |     | CDR2 |     |
|-----|-----|-----|-----|-----|-----|-----|-----|-----|-----|-----|-----|-----|-----|-----|
|     | Q   | Q   | K   | P   | G   | Q   | P   | P   | K   | L   | L   | I   | Y   | L   | A |
| 181 | CAA | CAG | AAA | CCA | GGA | CAG | CCA | CCC | AAA | CTC | CTC | ATC | TAT | CTT | GCA |

|     |     | CDR2 |     |     |     |     |     | FR3 |     |     |     |     |     |
|-----|-----|-----|-----|-----|-----|-----|-----|-----|-----|-----|-----|-----|-----|-----|
|     | S   | N   | L   | E   | S   | G   | V   | P   | A   | R   | F   | S   | G   | S   | G |
| 226 | TCC | AAC | CTA | GAA | TCT | GGG | GTC | CCT | GCC | AGG | TTC | AGT | GGC | AGT | GGG |

|     |     |     |     |     |     | FR3 |     |     |     |     |     |     |     |     |
|-----|-----|-----|-----|-----|-----|-----|-----|-----|-----|-----|-----|-----|-----|-----|
|     | S   | G   | T   | D   | F   | T   | L   | N   | I   | H   | P   | V   | E   | E   | E |
| 271 | TCT | GGG | ACA | GAC | TTC | ACC | CTC | AAC | ATC | CAT | CCT | GTG | GAG | GAG | GAG |

|     |     | FR3 |     |     |     |     |     | CDR3 |     |     |     |     |     |
|-----|-----|-----|-----|-----|-----|-----|-----|-----|-----|-----|-----|-----|-----|-----|
|     | D   | A   | A   | T   | Y   | Y   | C   | Q   | H   | S   | R   | E   | L   | P   | F |
| 316 | GAT | GCT | GCA | ACC | TAT | TAC | TGT | CAG | CAC | AGT | AGG | GAG | CTT | CCA | TTC |

|     | CDR3 |     |     |     | FR4 |     |     |     |     |     |     | C kappa |     |
|-----|-----|-----|-----|-----|-----|-----|-----|-----|-----|-----|-----|-----|-----|-----|
|     | T   | F   | G   | S   | G   | T   | K   | L   | E   | I   | K   | R   | A   | D   | A |
| 361 | ACG | TTC | GGC | TCG | GGG | ACA | AAG | TTG | GAA | ATA | AAA | CGG | GCT | GAT | GCT |

|     |     |     |     |     |     |     | C kappa |     |     |     |     |     |     |     |
|-----|-----|-----|-----|-----|-----|-----|-----|-----|-----|-----|-----|-----|-----|-----|
|     | A   | P   | T   | V   | S   | I   | F   | P   | P   | S   | S   | E   | Q   | L   | T |
| 406 | GCA | CCA | ACT | GTA | TCC | ATC | TTC | CCA | CCA | TCC | AGT | GAG | CAG | TTA | ACA |

|     |     |     |     |     |     |     | C kappa |     |     |     |     |     |     |     |
|-----|-----|-----|-----|-----|-----|-----|-----|-----|-----|-----|-----|-----|-----|-----|
|     | S   | G   | G   | A   | S   | V   | V   | C   | F   | L   | N   | N   | F   | Y   | P |
| 451 | TCT | GGA | GGT | GCC | TCA | GTC | GTG | TGC | TTC | TTG | AAC | AAC | TTC | TAC | CCC |

|     |     |     |     |     |     |     | C kappa |     |     |     |     |     |     |     |
|-----|-----|-----|-----|-----|-----|-----|-----|-----|-----|-----|-----|-----|-----|-----|
|     | K   | D   | I   | N   | V   | K   | W   | K   | I   | D   | G   | S   | E   | R   | Q |
| 496 | AAA | GAC | ATC | AAT | GTC | AAG | TGG | AAG | ATT | GAT | GGC | AGT | GAA | CGA | CAA |

|     |     |     |     |     |     |     | C kappa |     |     |     |     |     |     |     |
|-----|-----|-----|-----|-----|-----|-----|-----|-----|-----|-----|-----|-----|-----|-----|
|     | N   | G   | V   | L   | N   | S   | W   | T   | D   | Q   | D   | S   | K   | D   | S |
| 541 | AAT | GGC | GTC | CTG | AAC | AGT | TGG | ACT | GAT | CAG | GAC | AGC | AAA | GAC | AGC |

FIG. 3 (continued)

|     |     | T   | Y   | S   | M   | S   | S   | T   | L   | T   | L   | T   | K   | D   | E   | Y   |
|-----|-----|-----|-----|-----|-----|-----|-----|-----|-----|-----|-----|-----|-----|-----|-----|-----|
|     |     |     |     |     |     |     |     | *C kappa* | | | | | | | | |
| 586 | ACC | TAC | AGC | ATG | AGC | AGC | ACC | CTC | ACG | TTG | ACC | AAG | GAC | GAG | TAT |

|     | E   | R   | H   | N   | S   | Y   | T   | C   | E   | A   | T   | H   | K   | T   | S   |
|-----|-----|-----|-----|-----|-----|-----|-----|-----|-----|-----|-----|-----|-----|-----|-----|
|     |     |     |     |     | *C kappa* | | | | | | | | | | |
| 631 | GAA | CGA | CAT | AAC | AGC | TAT | ACC | TGT | GAG | GCC | ACT | CAC | AAG | ACA | TCA |

|     | T   | S   | P   | I   | V   | K   | S   | F   | N   | R   | N   | E   | C   |     |
|-----|-----|-----|-----|-----|-----|-----|-----|-----|-----|-----|-----|-----|-----|-----|
|     |     |     |     | *C kappa* | | | | | | | | | | *Stop* |
| 676 | ACT | TCA | CCC | ATT | GTC | AAG | AGC | TTC | AAC | AGG | AAT | GAG | TGT | TAG |

FIG. 4A

|  | | | | | | | Leader Sequence | | | | | | | |
|---|---|---|---|---|---|---|---|---|---|---|---|---|---|---|
|  | M | D | F | G | L | I | F | F | I | V | A | L | L | K | G |
| 1 | ATG | GAT | TTT | GGG | CTG | ATT | TTT | TTT | ATT | GTT | GCT | CTT | TTA | AAA | GGG |

|  | Leader Seq. | | | | | | | FR1 | | | | | | |
|---|---|---|---|---|---|---|---|---|---|---|---|---|---|---|
|  | V | Q | C | E | V | K | L | L | E | S | G | G | G | L | V |
| 46 | GTC | CAG | TGT | GAG | GTG | AAG | CTT | CTC | GAG | TCT | GGA | GGT | GGC | CTG | GTG |

|  | | | | | | | FR1 | | | | | | | |
|---|---|---|---|---|---|---|---|---|---|---|---|---|---|---|
|  | Q | P | G | G | S | L | K | L | S | C | A | A | S | G | F |
| 91 | CAG | CCT | GGA | GGA | TCC | CTG | AAA | CTC | TCC | TGT | GCA | GCC | TCA | GGA | TTC |

|  | | FR1 | | | CDR1 | | | | | FR2 | | | |
|---|---|---|---|---|---|---|---|---|---|---|---|---|---|---|
|  | D | F | S | R | Y | W | M | S | W | V | R | Q | A | P | G |
| 136 | GAT | TTC | AGT | AGA | TAC | TGG | ATG | AGT | TGG | GTC | CGG | CAG | GCT | CCA | GGG |

|  | | | FR2 | | | | | | | CDR2 | | | |
|---|---|---|---|---|---|---|---|---|---|---|---|---|---|---|
|  | K | G | L | E | W | I | G | E | I | N | P | T | S | S | T |
| 181 | AAA | GGG | CTA | GAA | TGG | ATT | GGA | GAG | ATT | AAT | CCA | ACT | AGC | AGT | ACG |

|  | | | | CDR2 | | | | | | | FR3 | | |
|---|---|---|---|---|---|---|---|---|---|---|---|---|---|---|
|  | I | N | F | T | P | S | L | K | D | K | V | F | I | S | R |
| 226 | ATA | AAC | TTT | ACG | CCA | TCT | CTA | AAG | GAT | AAA | GTC | TTC | ATC | TCC | AGA |

|  | | | | | | | FR3 | | | | | | | |
|---|---|---|---|---|---|---|---|---|---|---|---|---|---|---|
|  | D | N | A | K | N | T | L | Y | L | Q | M | S | K | V | R |
| 271 | GAC | AAC | GCC | AAA | AAT | ACG | CTG | TAC | CTG | CAA | ATG | AGC | AAA | GTG | AGA |

|  | | | | | FR3 | | | | | | | CDR3 | | |
|---|---|---|---|---|---|---|---|---|---|---|---|---|---|---|
|  | S | E | D | T | A | L | Y | Y | C | A | R | G | N | Y | Y |
| 316 | TCT | GAG | GAC | ACA | GCC | CTT | TAT | TAC | TGT | GCA | AGA | GGG | AAC | TAC | TAT |

|  | | | CDR3 | | | | | | | FR4 | | | |
|---|---|---|---|---|---|---|---|---|---|---|---|---|---|---|
|  | R | Y | G | D | A | M | D | Y | W | G | Q | G | T | S | V |
| 361 | AGG | TAC | GGA | GAT | GCT | ATG | GAC | TAC | TGG | GGT | CAA | GGA | ACC | TCA | GTC |

|  | | FR4 | | | Constant region | | | | | | | | | |
|---|---|---|---|---|---|---|---|---|---|---|---|---|---|---|
|  | T | V | S | S | A | K | T | T | P | P | S | V | Y | P | L |
| 406 | ACC | GTC | TCC | TCA | GCC | AAA | ACG | ACA | CCC | CCA | TCT | GTC | TAT | CCA | CTG |

|  | | | | | Constant region | | | | | | | | | |
|---|---|---|---|---|---|---|---|---|---|---|---|---|---|---|
|  | A | P | G | S | A | A | Q | T | D141 | S | M | V | T | L | G |
| 451 | GCC | CCT | GGA | TCT | GCT | GCC | CAA | ACT | AAC | TCC | ATG | GTG | ACC | CTG | GGA |

|  | | | | | Constant region | | | | | | | | | |
|---|---|---|---|---|---|---|---|---|---|---|---|---|---|---|
|  | C | L | V | K | G | Y | F | P | E | P | V | T | V | T | W |
| 496 | TGC | CTG | GTC | AAG | GGC | TAT | TTC | CCT | GAG | CCA | GTG | ACA | GTG | ACC | TGG |

|  | | | | | Constant region | | | | | | | | | |
|---|---|---|---|---|---|---|---|---|---|---|---|---|---|---|
|  | N | S | G | S | L | S | S | G | V | H | T | F | P | A | V |
| 541 | AAC | TCT | GGA | TCC | CTG | TCC | AGC | GGT | GTG | CAC | ACC | TTC | CCA | GCT | GTC |

FIG. 4A (continued)

|  |  |  |  |  |  |  | Constant region |  |  |  |  |  |  |  |
|---|---|---|---|---|---|---|---|---|---|---|---|---|---|---|
|  | L | Q | S | D | L | Y | T | L | S | S | S | V | T | V | P |
| 586 | CTG | CAG | TCT | GAC | CTC | TAC | ACT | CTG | AGC | AGC | TCA | GTG | ACT | GTC | CCC |

|  |  |  |  |  |  |  | Constant region |  |  |  |  |  |  |  |
|---|---|---|---|---|---|---|---|---|---|---|---|---|---|---|
|  | S | S | T | W | P | S | E | T | V | T | C | N | V | A | H |
| 631 | TCC | AGC | ACC | TGG | CCC | AGC | GAG | ACC | GTC | ACC | TGC | AAC | GTT | GCC | CAC |

|  |  |  |  |  |  |  | Constant region |  |  |  |  |  |  |  |
|---|---|---|---|---|---|---|---|---|---|---|---|---|---|---|
|  | P | A | S | S | T | K | V | D | K | K | I | V | P | R | D |
| 676 | CCG | GCC | AGC | AGC | ACC | AAG | GTG | GAC | AAG | AAA | ATT | GTG | CCC | AGG | GAT |

|  |  |  |  |  |  |  | Constant region |  |  |  |  |  |  |  |
|---|---|---|---|---|---|---|---|---|---|---|---|---|---|---|
|  | C | G | C | K | P | C | I | C | T | V | P | E | V | S | S |
| 721 | TGT | GGT | TGT | AAG | CCT | TGC | ATA | TGT | ACA | GTC | CCA | GAA | GTA | TCA | TCT |

|  |  |  |  |  |  |  | Constant region |  |  |  |  |  |  |  |
|---|---|---|---|---|---|---|---|---|---|---|---|---|---|---|
|  | V | F | I | F | P | P | K | P | K | D | V | L | T | I | T |
| 766 | GTC | TTC | ATC | TTC | CCC | CCA | AAG | CCC | AAG | GAT | GTG | CTC | ACC | ATT | ACT |

|  |  |  |  |  |  |  | Constant region |  |  |  |  |  |  |  |
|---|---|---|---|---|---|---|---|---|---|---|---|---|---|---|
|  | L | T | P | K | V | T | C | V | V | V | D | I | S | K | D |
| 811 | CTG | ACT | CCT | AAG | GTC | ACG | TGT | GTT | GTG | GTA | GAC | ATC | AGC | AAG | GAT |

|  |  |  |  |  |  |  | Constant region |  |  |  |  |  |  |  |
|---|---|---|---|---|---|---|---|---|---|---|---|---|---|---|
|  | D | P | E | V | Q | F | S | W | F | V | D | D | V | E | V |
| 856 | GAT | CCC | GAG | GTC | CAG | TTC | AGC | TGG | TTT | GTA | GAT | GAT | GTG | GAG | GTG |

|  |  |  |  |  |  |  | Constant region |  |  |  |  |  |  |  |
|---|---|---|---|---|---|---|---|---|---|---|---|---|---|---|
|  | H | T | A | Q | T | Q | P | R | E | E | Q | F | N | S | T |
| 901 | CAC | ACA | GCT | CAG | ACG | CAA | CCC | CGG | GAG | GAG | CAG | TTC | AAC | AGC | ACT |

|  |  |  |  |  |  |  | Constant region |  |  |  |  |  |  |  |
|---|---|---|---|---|---|---|---|---|---|---|---|---|---|---|
|  | F | R | S | V | S | E | L | P | I | M | H | Q | D | W | L |
| 946 | TTC | CGC | TCA | GTC | AGT | GAA | CTT | CCC | ATC | ATG | CAC | CAG | GAC | TGG | CTC |

|  |  |  |  |  |  |  | Constant region |  |  |  |  |  |  |  |
|---|---|---|---|---|---|---|---|---|---|---|---|---|---|---|
|  | N | G | K | E | F | K | C | R | V | N | S | A | A | F | P |
| 991 | AAT | GGC | AAG | GAG | TTC | AAA | TGC | AGG | GTC | AAC | AGT | GCA | GCT | TTC | CCT |

|  |  |  |  |  |  |  | Constant region |  |  |  |  |  |  |  |
|---|---|---|---|---|---|---|---|---|---|---|---|---|---|---|
|  | A | P | I | E | K | T | I | S | K | T | K | G | R | P | K |
| 1036 | GCC | CCC | ATC | GAG | AAA | ACC | ATC | TCC | AAA | ACC | AAA | GGC | AGA | CCG | AAG |

|  |  |  |  |  |  |  | Constant region |  |  |  |  |  |  |  |
|---|---|---|---|---|---|---|---|---|---|---|---|---|---|---|
|  | A | P | Q | V | Y | T | I | P | P | P | K | E | Q | M | A |
| 1081 | GCT | CCA | CAG | GTG | TAC | ACC | ATT | CCA | CCT | CCC | AAG | GAG | CAG | ATG | GCC |

|  |  |  |  |  |  |  | Constant region |  |  |  |  |  |  |  |
|---|---|---|---|---|---|---|---|---|---|---|---|---|---|---|
|  | K | D | K | V | S | L | T | C | M | I | T | D | F | F | P |
| 1126 | AAG | GAT | AAA | GTC | AGT | CTG | ACC | TGC | ATG | ATA | ACA | GAC | TTC | TTC | CCT |

FIG. 4A (continued)

|      |     |     |     |     |     | *Constant region* |     |     |     |     |     |     |     |     |
|------|-----|-----|-----|-----|-----|-----|-----|-----|-----|-----|-----|-----|-----|-----|
|      | E   | D   | I   | T   | V   | E   | W   | Q   | W   | N   | G   | Q   | P   | A   | E   |
| 1171 | GAA | GAC | ATT | ACT | GTG | GAG | TGG | CAG | TGG | AAT | GGG | CAG | CCA | GCG | GAG |

|      |     |     |     |     |     | *Constant region* |     |     |     |     |     |     |     |     |
|------|-----|-----|-----|-----|-----|-----|-----|-----|-----|-----|-----|-----|-----|-----|
|      | N   | Y   | K   | N   | T   | Q   | P   | I   | M   | D   | T   | D   | G   | S   | Y   |
| 1216 | AAC | TAC | AAG | AAC | ACT | CAG | CCC | ATC | ATG | GAC | ACA | GAT | GGC | TCT | TAC |

|      |     |     |     |     |     | *Constant region* |     |     |     |     |     |     |     |     |
|------|-----|-----|-----|-----|-----|-----|-----|-----|-----|-----|-----|-----|-----|-----|
|      | F   | V   | Y   | S   | K   | L   | N   | V   | Q   | K   | S   | N   | W   | E   | A   |
| 1261 | TTC | GTC | TAC | AGC | AAG | CTC | AAT | GTG | CAG | AAG | AGC | AAC | TGG | GAG | GCA |

|      |     |     |     |     |     | *Constant region* |     |     |     |     |     |     |     |     |
|------|-----|-----|-----|-----|-----|-----|-----|-----|-----|-----|-----|-----|-----|-----|
|      | G   | N   | T   | F   | T   | C   | S   | V   | L   | H   | E   | G   | L   | H   | N   |
| 1306 | GGA | AAT | ACT | TTC | ACC | TGC | TCT | GTG | TTA | CAT | GAG | GGC | CTG | CAC | AAC |

|      |     |     |     |     |     | *Constant region* |     |     |     |     |     | *Stop* |     |
|------|-----|-----|-----|-----|-----|-----|-----|-----|-----|-----|-----|-----|-----|-----|
|      | H   | H   | T   | E   | K   | S   | L   | S   | H   | S   | P   | G   | K   | *   |
| 1351 | CAC | CAT | ACT | GAG | AAG | AGC | CTC | TCC | CAC | TCT | CCT | GGT | AAA | TGA |

FIG. 4B

|     | Leader Sequence |     |     |     |     |     |     |     |     |     |     |     |     |     |     |
|-----|-----|-----|-----|-----|-----|-----|-----|-----|-----|-----|-----|-----|-----|-----|-----|
|     | M | D | F | G | L | I | F | F | I | V | A | L | L | K | G |
| 1   | ATG | GAT | TTT | GGG | CTG | ATT | TTT | TTT | ATT | GTT | GCT | CTT | TTA | AAA | GGG |

|     | Leader Seq. | | | | | | FR1 | | | | | | | | |
|-----|-----|-----|-----|-----|-----|-----|-----|-----|-----|-----|-----|-----|-----|-----|-----|
|     | V | Q | C | E | V | K | L | L | E | S | G | G | G | L | V |
| 46  | GTC | CAG | TGT | GAG | GTG | AAG | CTT | CTC | GAG | TCT | GGA | GGT | GGC | CTG | GTG |

|     | FR1 | | | | | | | | | | | | | | |
|-----|-----|-----|-----|-----|-----|-----|-----|-----|-----|-----|-----|-----|-----|-----|-----|
|     | Q | P | G | G | S | L | K | L | S | C | A | A | S | G | F |
| 91  | CAG | CCT | GGA | GGA | TCC | CTG | AAA | CTC | TCC | TGT | GCA | GCC | TCA | GGA | TTC |

|     | FR1 | | | CDR1 | | | | | FR2 | | | | | | |
|-----|-----|-----|-----|-----|-----|-----|-----|-----|-----|-----|-----|-----|-----|-----|-----|
|     | D | F | S | R | Y | W | M | S | W | V | R | Q | A | P | G |
| 136 | GAT | TTC | AGT | AGA | TAC | TGG | ATG | AGT | TGG | GTC | CGG | CAG | GCT | CCA | GGG |

|     | FR2 | | | | | | | | CDR2 | | | | | | |
|-----|-----|-----|-----|-----|-----|-----|-----|-----|-----|-----|-----|-----|-----|-----|-----|
|     | K | G | L | E | W | I | G | E | I | N | P | T | S | S | T |
| 181 | AAA | GGG | CTA | GAA | TGG | ATT | GGA | GAG | ATT | AAT | CCA | ACT | AGC | AGT | ACG |

|     | | | | CDR2 | | | | | | | FR3 | | | | |
|-----|-----|-----|-----|-----|-----|-----|-----|-----|-----|-----|-----|-----|-----|-----|-----|
|     | I | N | F | T | P | S | L | K | D | K | V | F | I | S | R |
| 226 | ATA | AAC | TTT | ACG | CCA | TCT | CTA | AAG | GAT | AAA | GTC | TTC | ATC | TCC | AGA |

|     | | | | | | | FR3 | | | | | | | | |
|-----|-----|-----|-----|-----|-----|-----|-----|-----|-----|-----|-----|-----|-----|-----|-----|
|     | D | N | A | K | N | T | L | Y | L | Q | M | S | K | V | R |
| 271 | GAC | AAC | GCC | AAA | AAT | ACG | CTG | TAC | CTG | CAA | ATG | AGC | AAA | GTG | AGA |

|     | | | | | | FR3 | | | | | | | CDR3 | | |
|-----|-----|-----|-----|-----|-----|-----|-----|-----|-----|-----|-----|-----|-----|-----|-----|
|     | S | E | D | T | A | L | Y | Y | C | A | R | G | N | Y | Y |
| 316 | TCT | GAG | GAC | ACA | GCC | CTT | TAT | TAC | TGT | GCA | AGA | GGG | AAC | TAC | TAT |

|     | | | | CDR3 | | | | | | | FR4 | | | | |
|-----|-----|-----|-----|-----|-----|-----|-----|-----|-----|-----|-----|-----|-----|-----|-----|
|     | R | Y | G | D | A | M | D | Y | W | G | Q | G | T | S | V |
| 361 | AGG | TAC | GGA | GAT | GCT | ATG | GAC | TAC | TGG | GGT | CAA | GGA | ACC | TCA | GTC |

|     | FR4 | | | | | Constant region | | | | | | | | | |
|-----|-----|-----|-----|-----|-----|-----|-----|-----|-----|-----|-----|-----|-----|-----|-----|
|     | T | V | S | S | A | K | T | T | P | P | S | V | Y | P | L |
| 406 | ACC | GTC | TCC | TCA | GCC | AAA | ACG | ACA | CCC | CCA | TCT | GTC | TAT | CCA | CTG |

|     | | | | | Constant region | | | | | | | | | | |
|-----|-----|-----|-----|-----|-----|-----|-----|-----|-----|-----|-----|-----|-----|-----|-----|
|     | A | P | G | S | A | A | Q | T | N | S | M | V | T | L | G |
| 451 | GCC | CCT | GGA | TCT | GCT | GCC | CAA | ACT | AAC | TCC | ATG | GTG | ACC | CTG | GGA |

|     | | | | | Constant region | | | | | | | | | | |
|-----|-----|-----|-----|-----|-----|-----|-----|-----|-----|-----|-----|-----|-----|-----|-----|
|     | C | L | V | K | G | Y | F | P | E | P | V | T | V | T | W |
| 496 | TGC | CTG | GTC | AAG | GGC | TAT | TTC | CCT | GAG | CCA | GTG | ACA | GTG | ACC | TGG |

|     | | | | | Constant region | | | | | | | | | | |
|-----|-----|-----|-----|-----|-----|-----|-----|-----|-----|-----|-----|-----|-----|-----|-----|
|     | N | S | G | S | L | S | S | G | V | H | T | F | P | A | V |
| 541 | AAC | TCT | GGA | TCC | CTG | TCC | AGC | GGT | GTG | CAC | ACC | TTC | CCA | GCT | GTC |

FIG. 4B (continued)

|  |  |  |  |  |  |  |  |  | Constant region |  |  |  |  |  |
|---|---|---|---|---|---|---|---|---|---|---|---|---|---|---|
|  | L | Q | S | D | L | Y | T | L | S | S | S | V | T | V | P |
| 586 | CTG | CAG | TCT | GAC | CTC | TAC | ACT | CTG | AGC | AGC | TCA | GTG | ACT | GTC | CCC |

|  |  |  |  |  |  |  | Constant region |  |  |  |  |  |  |  |
|---|---|---|---|---|---|---|---|---|---|---|---|---|---|---|
|  | S | S | T | W | P | S | E | T | V | T | C | N | V | A | H |
| 631 | TCC | AGC | ACC | TGG | CCC | AGC | GAG | ACC | GTC | ACC | TGC | AAC | GTT | GCC | CAC |

|  |  |  |  |  |  |  | Constant region |  |  |  |  |  |  |  |
|---|---|---|---|---|---|---|---|---|---|---|---|---|---|---|
|  | P | A | S | S | T | K | V | D | K | K | I | V | P | R | D |
| 676 | CCG | GCC | AGC | AGC | ACC | AAG | GTG | GAC | AAG | AAA | ATT | GTG | CCC | AGG | GAT |

|  |  |  |  |  |  |  | Constant region |  |  |  |  |  |  |  |
|---|---|---|---|---|---|---|---|---|---|---|---|---|---|---|
|  | C | G | C | K | P | C | I | C | T | V | P | E | V | S | S |
| 721 | TGT | GGT | TGT | AAG | CCT | TGC | ATA | TGT | ACA | GTC | CCA | GAA | GTA | TCA | TCT |

|  |  |  |  |  |  |  | Constant region |  |  |  |  |  |  |  |
|---|---|---|---|---|---|---|---|---|---|---|---|---|---|---|
|  | V | F | I | F | P | P | K | P | K | D | V | L | T | I | T |
| 766 | GTC | TTC | ATC | TTC | CCC | CCA | AAG | CCC | AAG | GAT | GTG | CTC | ACC | ATT | ACT |

|  |  |  |  |  |  |  | Constant region |  |  |  |  |  |  |  |
|---|---|---|---|---|---|---|---|---|---|---|---|---|---|---|
|  | L | T | P | K | V | T | C | V | V | V | D | I | S | K | D |
| 811 | CTG | ACT | CCT | AAG | GTC | ACG | TGT | GTT | GTG | GTA | GAC | ATC | AGC | AAG | GAT |

|  |  |  |  |  |  |  | Constant region |  |  |  |  |  |  |  |
|---|---|---|---|---|---|---|---|---|---|---|---|---|---|---|
|  | D | P | E | V | Q | F | S | W | F | V | D | D | V | E | V |
| 856 | GAT | CCC | GAG | GTC | CAG | TTC | AGC | TGG | TTT | GTA | GAT | GAT | GTG | GAG | GTG |

|  |  |  |  |  |  |  | Constant region |  |  |  |  |  |  |  |
|---|---|---|---|---|---|---|---|---|---|---|---|---|---|---|
|  | H | T | A | Q | T | Q | P | R | E | E | Q | F | N | S | T |
| 901 | CAC | ACA | GCT | CAG | ACG | CAA | CCC | CGG | GAG | GAG | CAG | TTC | AAC | AGC | ACT |

|  |  |  |  |  |  |  | Constant region |  |  |  |  |  |  |  |
|---|---|---|---|---|---|---|---|---|---|---|---|---|---|---|
|  | F | R | S | V | S | E | L | P | I | M | H | Q | D | W | L |
| 946 | TTC | CGC | TCA | GTC | AGT | GAA | CTT | CCC | ATC | ATG | CAC | CAG | GAC | TGG | CTC |

|  |  |  |  |  |  |  | Constant region |  |  |  |  |  |  |  |
|---|---|---|---|---|---|---|---|---|---|---|---|---|---|---|
|  | N | G | K | E | F | K | C | R | V | N | S | A | A | F | P |
| 991 | AAT | GGC | AAG | GAG | TTC | AAA | TGC | AGG | GTC | AAC | AGT | GCA | GCT | TTC | CCT |

|  |  |  |  |  |  |  | Constant region |  |  |  |  |  |  |  |
|---|---|---|---|---|---|---|---|---|---|---|---|---|---|---|
|  | A | P | I | E | K | T | I | S | K | T | K | G | R | P | K |
| 1036 | GCC | CCC | ATC | GAG | AAA | ACC | ATC | TCC | AAA | ACC | AAA | GGC | AGA | CCG | AAG |

|  |  |  |  |  |  |  | Constant region |  |  |  |  |  |  |  |
|---|---|---|---|---|---|---|---|---|---|---|---|---|---|---|
|  | A | P | Q | V | Y | T | I | P | P | P | K | E | Q | M | A |
| 1081 | GCT | CCA | CAG | GTG | TAC | ACC | ATT | CCA | CCT | CCC | AAG | GAG | CAG | ATG | GCC |

|  |  |  |  |  |  |  | Constant region |  |  |  |  |  |  |  |
|---|---|---|---|---|---|---|---|---|---|---|---|---|---|---|
|  | K | D | K | V | S | L | T | C | M | I | T | D | F | F | P |
| 1126 | AAG | GAT | AAA | GTC | AGT | CTG | ACC | TGC | ATG | ATA | ACA | GAC | TTC | TTC | CCT |

FIG. 4B (continued)

|  |  |  | | | | Constant region | | | | | | | | |
|---|---|---|---|---|---|---|---|---|---|---|---|---|---|---|
|  | E | D | I | T | V | E | W | Q | W | N | G | Q | P | A | E |
| 1171 | GAA | GAC | ATT | ACT | GTG | GAG | TGG | CAG | TGG | AAT | GGG | CAG | CCA | GCG | GAG |

|  |  |  | | | | Constant region | | | | | | | | |
|---|---|---|---|---|---|---|---|---|---|---|---|---|---|---|
|  | N | Y | K | N | T | Q | P | I | M | D | T | D | G | S | Y |
| 1216 | AAC | TAC | AAG | AAC | ACT | CAG | CCC | ATC | ATG | GAC | ACA | GAT | GGC | TCT | TAC |

|  |  |  | | | | Constant region | | | | | | | | |
|---|---|---|---|---|---|---|---|---|---|---|---|---|---|---|
|  | F | V | Y | S | K | L | N | V | Q | K | S | N | W | E | A |
| 1261 | TTC | GTC | TAC | AGC | AAG | CTC | AAT | GTG | CAG | AAG | AGC | AAC | TGG | GAG | GCA |

|  |  |  | | | | Constant region | | | | | | | | |
|---|---|---|---|---|---|---|---|---|---|---|---|---|---|---|
|  | G | N | T | F | T | C | S | V | L | H | E | G | L | H | N |
| 1306 | GGA | AAT | ACT | TTC | ACC | TGC | TCT | GTG | TTA | CAT | GAG | GGC | CTG | CAC | AAC |

|  |  |  | | | Constant region | | | | | | | | Stop | |
|---|---|---|---|---|---|---|---|---|---|---|---|---|---|---|
|  | H | H | T | E | K | S | L | S | H | S | P | G | K | * |
| 1351 | CAC | CAT | ACT | GAG | AAG | AGC | CTC | TCC | CAC | TCT | CCT | GGT | AAA | TGA |

STABILIZED RADIO-LABELED ANTI-CD45 IMMUNOGLOBULIN COMPOSITIONS

CROSS REFERENCE TO RELATED APPLICATION

This application is a continuation of U.S. patent application Ser. No. 15/603,817, filed May 24, 2017 know U.S. Pat. No. 10,420,851), which is a continuation-in-part of International Application PCT/US17/21076, filed Mar. 7, 2017, which claims priority of U.S. Provisional Application No. 62/304,537, filed Mar. 7, 2016, the contents of each of which are incorporated herein by reference in their entirety.

REFERENCE TO A SEQUENCE LISTING

This application contains a Sequence Listing in computer readable form, which is herein incorporated by reference.

FIELD OF THE INVENTION

The present invention relates to compositions of a radio-iodinated murine monoclonal antibody specific for the CD45 antigen, and more particularly, compositions comprising the radio-iodinated murine monoclonal antibody and one or more excipients that stabilize the antibody against radiolytic decomposition.

BACKGROUND OF THE INVENTION

The CD45 antigen is a member of the protein tyrosine phosphatase (PTP) family and is a 180-240 kD transmembrane glycoprotein. It is also known as the leukocyte common antigen (LCA), T200, or Ly-5. CD45 plays a key role in T-cell and B-cells receptor signal transduction. Different isoforms of CD45 exist due to variable splicing of its exons. These isoforms are very specific to the activation and maturation state of the cell as well as cell type. The various isoforms have the same trans-membrane and cytoplasmic segments, but different extra-cellular domains, and are differentially expressed on subpopulations of B- and T-cell lymphocytes. The primary ligands described for CD45 include galectin-1, CD1, CD2, CD3, CD4, TCR, CD22 and Thy-1.

Depending on which of the alternatively spliced exons (A, B or C) is recognized, antibodies restricted to recognizing one or the other isoform have been identified (termed CD45R). In addition, monoclonal antibodies (mAbs) binding an epitope common to all the different isoforms have also been identified. The mAbs designated CD45RA recognize the product of exon-A. The mAbs designated CD45RB recognize the product of exon-B. A third type of mAbs termed CD45RO (as exemplified by UCHL1) selectively bind to the 180 kD isoform (without any of the variable exons A, B or C) which is restricted to a subset of cortical thymocytes, activated T cells and memory cells, and is absent on B cells.

In general, all cells of hematopoietic origin, with the exception of mature erythrocytes and platelets, express CD45. High expression of CD45 is seen with most acute lymphoid and myeloid leukemias. Since CD45 is not found on tissues of non-hematopoietic origin, its specific expression in leukemia has made it a good target for developing therapeutics, including radio-immunotherapeutics. For example, CD45 is expressed at a density of approximately 200,000 to 300,000 sites per cell on circulating leukocytes and malignant B cells. One particular $^{131}$I-labeled anti-CD45 antibody, BC8, has been explored as a candidate radio-immunotherapeutic alone and in combination with chemotherapy or total body irradiation. The use of this $^{131}$I-anti-CD45 antibody for the treatment of subjects needing bone marrow transplant has also been explored.

A number of anti-CD45 antibodies are commercially available. These include human, mouse, rat, rabbit, canine antibodies and a host of related derived reagents, such as, conjugates with fluorophores, chromophores, biotin and dyes. These also include antibodies derived by the use of various epitopes, domains and regions of CD45 antigen. Several clones of the species-specific anti-CD45 antibody are also commercially available. A list of commercial suppliers of anti-CD45 antibodies include the following: eBioscience, Inc., San Diego, Calif., USA; Novus Biologicals, LLC, Littleton, Colo., USA; Bethyl Laboratories, Inc., Montgomery, Tex., USA; AbD Serotec/Bio-Rad Inc., Raleigh, N.C., USA; BD Biosciences, San Jose, Calif., USA; AbCam Inc., Cambridge, Mass., USA; Enzo Life Sciences, Inc., Farmingdale, N.Y., USA; R&D Systems Inc., Minneapolis, Minn., USA; EXBIO Praha, A. S., Vestec, Czech Republic; Life Technologies, Grand Island, N.Y.; and many more. A comprehensive list of suppliers can be accessed at the following web site:

http://www.biocompare.com/pfu/110447/soids/3537/Antibodies/CD45?vmpi_6408=1.

A search at this site for "CD45 antibody" performed on Sep. 25, 2014 came up with a total of 3,646 products that are available from 59 suppliers. It is evident that a number of anti-CD45 antibodies and related reagents are available with their own specific product characteristics such as species specificity and antigen heterogeneity, such as epitope or domain specificity.

While large numbers, varieties, and clones of anti-CD45 antibodies are available, none is structurally well described. For use as a therapeutic agent, it would be advantageous to properly describe an anti-CD45 antibody in order to develop the anti-CD45 antibody into a therapeutic for the treatment of human indications of hematopoietic malignancies.

Among several clones of the anti-CD45 murine antibody, BC8 recognizes all the human isoforms of the CD45 antigen. The potential applications of the BC8 antibody for clinical use, including the treatment of certain kinds of human lymphomas, are well defined in the literature of the past 20-25 years. Despite this, the structural composition and characterization of this isolated BC8 clone for use as a human therapeutic has not been adequately described.

Only a partial amino acid sequence from a BC8 clone has been described as being used in making a single chain construct with streptavidin. In this construct, certain regions corresponding to the putative variable regions of the light chain (LC) and heavy chain (HC) were fused together with the streptavidin sequence. Therefore, some 110-120 amino acid stretches related to the LC and HC of BC8 were used in this particular context which were indirectly identified by the methods of reverse transcription-PCR (RT-PCR).

As such, the complete structural composition of the BC8 mAb has not been described and characterized.

As indicated above, the BC8 antibody has been shown to bind to all the isoforms of human CD45, and thus provides an excellent target for the development of therapeutics for certain human malignancies of hematopoietic origin, including lymphomas. While radiolabelling of BC8 for targeted treatment of such malignancies has been explored, none of the prior art has been able to achieve radiolabelling efficiencies suitable for its efficient and cost effective use as a therapeutic. Furthermore, BC8 radiolabelled with $^{131}$I has a short half-life (the half-life of $^{131}$I is 8.02 days), and must be made and shipped to clinical sites on demand, which impedes its wider use as a therapeutic.

Radio-iodinated antibodies can undergo auto-radiolysis, due to radiation energy decay and associated free radical mechanisms. This can dramatically reduce the antibodies' immune-reactivity, rendering them less effective and thus unsafe for therapeutic use. Moreover, free radical reactivity towards certain amino acid residues (e.g., Tyr, Trp, His, Met and Cys) in a protein can affect the solution stability of a protein-based radiopharmaceutical composition. Thus, stabilizing target-specific radiopharmaceutical compositions remains a challenge in their development.

New compositions and methods are needed to stabilize $^{131}$I-anti-CD45 immunoglobulins, such as BC8, thereby prolonging shelf life and improving human therapeutic potential.

SUMMARY OF THE INVENTION

The present invention relates to a stabilized composition comprising an isolated anti-CD45 immunoglobulin (e.g., BC8 mAb clone) in its $^{131}$I radiolabeled form, and its therapeutic uses. With its ability to bind all the isoforms of the CD45 antigen, BC8 is expected to accumulate a therapeutically high radiation dose specifically and preferentially at high-density CD45 antigen-bearing cells, such as lymphoma cells.

The present invention further relates to methods of radio-labeling the anti-CD45 antibody in a high radioactivity batch, such as up to 3,000 mCi, or even 5,000 mCi, as well as therapeutic and dosimetry dose formulations comprising the radio-iodinated antibody that are stabilized against radiolysis of the antibody.

As such, the present invention provides stabilized radio-iodinated anti-CD45 immunoglobulin compositions specific for targeting the CD45 antigen. Certain formulations may comprise 0.5% to 5.0% (w/v) of an excipient selected from the group consisting of ascorbic acid, polyvinylpyrrolidone (PVP), human serum albumin (HSA), a water-soluble salt of HSA, and mixtures thereof. Certain formulations may comprise 0.5-5% ascorbic acid; 0.5-4% polyvinylpyrrolidone (PVP); and 0.1-2 mg/mL of the radio-iodinated anti-CD45 antibody (e.g., BC8) in 50 mM PBS buffer, pH 7.

The heavy chain variable domain of the antibody may comprise an N-terminal sequence of SEQ ID NO:12 in combination with at least one complementarity determining region (CDR) selected from SEQ ID NO:6, SEQ ID NO:7, and SEQ ID NO:8; and the light chain variable domain may comprise an N-terminal sequence of SEQ ID NO:11 in combination with at least one CDR selected from SEQ ID NO:3, SEQ ID NO:4, and SEQ ID NO:5.

The heavy chain of the antibody may comprise a sequence of SEQ ID NO:14.

The present invention further provides a composition comprising: an anti-CD45 IgG monoclonal antibody, wherein the anti-CD45 IgG monoclonal antibody is labeled with radio-iodine; and at least one stabilizer (excipient) comprising 0.5 to 5% (w/v) of ascorbic acid, PVP, human serum albumin (HSA), or water soluble salts of HSA, or combinations thereof, preferably wherein the stabilizer is added during the purification of the $^{131}$I-labeled anti-CD45 IgG monoclonal antibody preparation.

According to certain aspects of the present invention, the stabilizer may be present in a w/v concentration range of 0.5 to 5% in an aqueous formulation comprising phosphate buffered saline, 50 mM pH 7 as a physiologically acceptable carrier or diluent.

The stabilizer may be ascorbic acid in a w/v concentration of 2.5% included immediately following the quenching of the radio-iodination reaction and before the purification of the radio-iodinated anti-CD45-immunoglobulin. Additionally, 2 to 4% (w/v) HSA may also be included along with ascorbic acid at the same step. The purification of this mixture using a desalting column may be performed with a pre-cooled mobile phase of PBS buffer (50 mM, pH 7) which is also supplemented with the 2.5% ascorbic acid or a mixture of 2.5% ascorbic acid plus 2 to 4% HSA (all w/v) as the case may be.

Furthermore, 2% (w/v) PVP may also be included in the purified $^{131}$I-anti-CD45-immunoglobulin as yet another stabilizer (excipient) providing stability to the labeled immunoglobulin against radiolysis.

It is also an objective of the present invention to provide, via a cocktail of excipients (stabilizers), stability of at least four days (i.e., the first three days at −20° C. and an additional day at room temperature) to a therapeutic dose formulation. Preferred stability-enhancing cocktails include w/v 2.5% ascorbic acid and 2% PVP; 2.5% ascorbic acid and 4% HSA; and 2.5% ascorbic acid, 4% HSA and 2% PVP (i.e., these cocktails yield immunoglobulin-containing compositions having the recited excipient concentrations).

It is yet another objective of the present invention to provide, via a cocktail of excipients, stability of at least seven days (i.e., the first six days at −20° C. and an additional day at room temperature) to a dosimetry dose formulation. Preferred stability-enhancing cocktails for dosimetry dose formulation include w/v 2.5% ascorbic acid and 2% PVP; 2.5% ascorbic acid and 4% HSA; and 2.5% ascorbic acid, 4% HSA, and 2% PVP. The stability-indicating assays include an iTLC (instant thin layer chromatography) assay, size exclusion chromatography-HPLC (SEC-HPLC) and a cell-specific binding-based immunoreactivity measurement assay.

It is yet a further objective of the present invention to provide methods for treating a subject (preferably human) afflicted with a hematologic malignancy, comprising administering to the subject an effective amount of the instant pharmaceutical composition, either alone or in conjunction with another form of treatment (e.g., a bone marrow transplant). In one embodiment, the hematologic malignancy is acute myeloid leukemia, myelodysplastic syndrome, acute lymphoblastic leukemia, Hodgkin's disease or non-Hodgkin's lymphoma. Also envisioned is a method for ablating bone marrow cells in a subject (preferably human) afflicted with leukemia prior to the subject's receiving a bone marrow transplant, comprising administering to the subject a therapeutically effective amount of the instant pharmaceutical composition. According to certain aspects of the present invention, the leukemia may be acute myeloid leukemia, and the subject may be human, relapsed or refractory, and at least 55 years old.

Also provided by the present invention are aqueous pharmaceutical compositions comprising an radio-labeled BC8 antibody; and a pharmaceutically acceptable carrier, wherein the radio-labeled BC8 antibody comprises a heavy chain having SEQ ID NO:14. The radio-label on the BC8 may comprise a radiotherapeutic effector molecule, wherein exemplary radiotherapeutic effector molecules include beta emitters such as, for example $^{131}$I, $^{90}$Y, $^{177}$Lu, $^{186}$Re, or $^{186}$Re, and gamma emitters such as, for example, $^{125}$I or $^{123}$I.

Also provided by the present invention are aqueous pharmaceutical compositions comprising an $^{131}$I-labeled BC8 antibody; and a pharmaceutically acceptable carrier, wherein the $^{131}$I-labeled BC8 antibody comprises a heavy chain having SEQ ID NO:14. Methods for treating a subject afflicted with a hematologic malignancy, include administering to the subject an effective amount of this aqueous pharmaceutical composition, either alone or in conjunction with another form of treatment.

Still further envisioned is a method for performing dosimetry on a subject (preferably human) afflicted with a hematologic malignancy comprising administering to the subject a dosimetrically effective amount of the instant pharmaceutical composition. In this invention, administering is preferably intravenous, and may also be, for example, intramuscular and subcutaneous.

Relating to the present invention are the sequence-related characteristics of the anti-CD45 immunoglobulin (i.e., BC8) in terms of the N-terminal sequences and the CDR sequences of its light chain and the heavy chain. For the light chain, these sequences are defined as: SEQ ID NO:11 as the N-terminal sequence, SEQ ID NO:3, SEQ ID NO:4 and SEQ ID NO:5 as, respectively, the CDR1, CDR2 and CDR3 regions. For the heavy chain, these sequences are defined as: SEQ ID NO:12 as the N-terminal sequence, SEQ ID NO:6, SEQ ID NO:7 and SEQ ID NO:8 as, respectively, the CDR1, CDR2 and CDR3 regions. The entire sequence of the light and the heavy chains of the anti-CD45 immunoglobulin, as elucidated by the related RT-PCR-derived cDNA construct and LC-MS/MS peptide mapping approaches, is also provided (SEQ ID NO:13 for the light chain and SEQ ID NO:14 and 15 for the heavy chain). It is possible that certain isomeric amino acid replacements with exact mass, such as Leu for Ile or vice versa, could be allowed in these sequences.

Embodiments disclosed herein define excipient-stabilized radio-iodinated anti-CD45 immunoglobulin compositions that are useful as radiotherapeutic agents for the treatment of malignancies of hematopoietic origin.

The objects of the present invention will be realized and attained by means of the combinations specifically outlined in the appended claims. The foregoing general description and the following detailed description and examples of this invention are provided to illustrate various aspects of the present invention, and by no means are to be viewed as limiting any of the described embodiments.

BRIEF DESCRIPTION OF THE DRAWINGS

FIG. 1 provides the sequence of the complementarity determining regions (CDRs), framework regions and variable domain sequences of the light chain (VL) and the heavy chain (VH) of the anti-CD45 mAb. The CDRs are in bold and underlined.

FIG. 2 provides the CDRs and the N-terminal sequence of the light chain and the heavy chain of anti-CD45 mAb.

FIG. 3 provides the entire nucleotide (SEQ ID NO:9) and amino acid (SEQ ID NO:13) sequence of the light chain of an anti-CD45-immunoglobulin.

FIG. 4A provides the entire nucleotide (SEQ ID NO:10) and actual amino acid (SEQ ID NO:14) sequence of the heavy chain of anti-CD45-immunoglobulin.

FIG. 4B provides the entire nucleotide (SEQ ID NO:10) and theoretical amino acid (SEQ ID NO:15) sequence of the heavy chain of anti-CD45-immunoglobulin.

DEFINITIONS AND ABBREVIATIONS

Figure 5A:
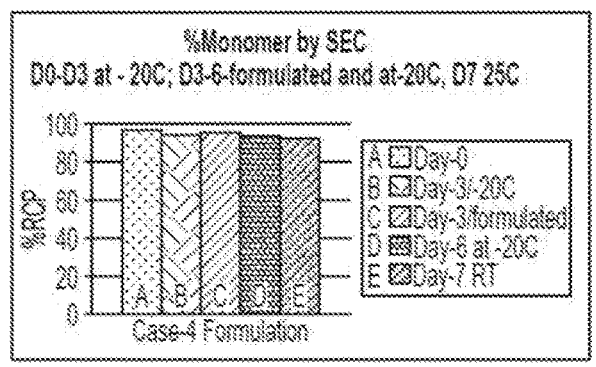
FIGS. 5A-5D provide bar graphs of stability test data for a 100 mCi dose of $^{131}$I-anti-CD45 immunoglobulin over a total period of seven days which included two freeze thaw cycles. Size exclusion-High performance liquid chromatography (SEC-HPLC) results showing percent product (FIG. 5A), percent free-$^{131}$I (FIG. 5D) and percent fraction of aggregates (FIG. 5C), and immunoreactivity results (FIG. 5B) are shown for various time points. The time points of this stability study and the formulation excipient composition were as follows: The radiolabeled anti-CD45 antibody initially formulated during the purification process contained 2.5% ascorbic acid and 4% HSA (both w/v) and was tested on day 0, and following its storage for 0-3 days at −20° C. On day-3 after thawing, it was further formulated with 2% (w/v) PVP and once again stored at −20° C. for three additional days. Both stability tests were performed on day-6 followed by storing the formulated product at room temperature for an additional 24 hours after which the stability tests were repeated.
Figure 5B:
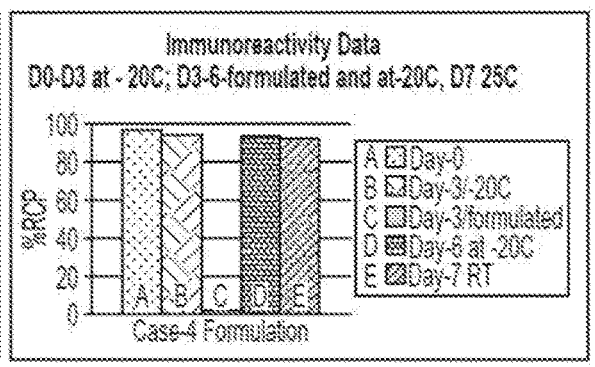
Figure 5C:
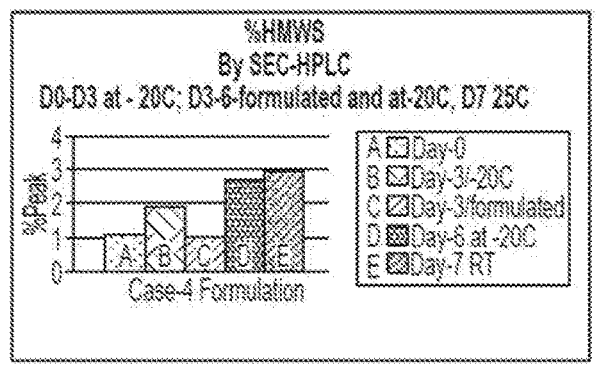
Figure 5D:
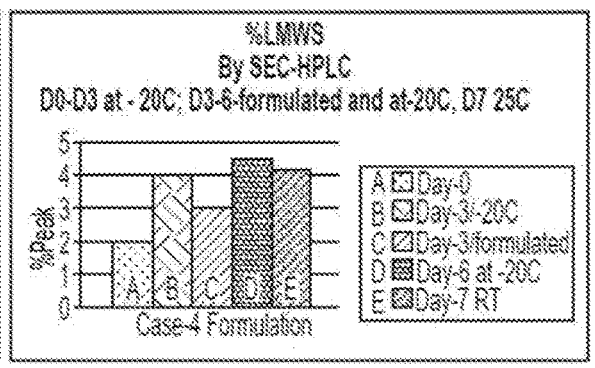

The following definitions and abbreviations have been used in describing this invention:
iTLC—instant thin layer chromatograph
IEF—isoelectric focusing
SDS-PAGE—sodium dodecyl sulfate—polyacrylamide gel electrophoresis
LC-MS/MS—liquid chromatography—tandem mass spectrometry
HSA—human serum albumin
PVP—polyvinylpyrrolidone (Povidone)
SEC-HPLC—size exclusion chromatography—High performance liquid chromatography
LMWS—low molecular weight species (Free-$^{131}$I)
BMWS—high molecular weight species (aggregates of antibody protein)

As used herein, the term "therapeutic dose" refers to an amount of radiolabeled immunoglobulin sufficient to provide a desired therapeutic radiation dose to the target tissue or organ upon administration to a subject. In one embodiment of the present invention, for example, this dose ranges between 100 to 1,500 mCi of $^{131}$I radioactivity.

As used herein, the term "dosimetry dose" refers to an amount of radiolabeled immunoglobulin sufficient to yield an in vivo biodistribution profile for various organs, and a pharmacokinetic profile, in a subject in need of therapy with the immunoglobulin, in order to help ascertain a subsequent therapeutic dose for the subject. In one embodiment of the present invention, for example, this dose ranges between five to 15 mCi of $^{131}$I radioactivity.

As used herein, the terms "antibody" and "immunoglobulin" are used interchangeably, and refer, for example, to full-length monoclonal antibodies and polyclonal antibodies. These include, for example, murine antibodies, human antibodies, humanized antibodies, chimeric antibodies, Fab fragments, F(ab')$_2$ fragments, antibody fragments with the desired biological activity, and epitope-binding fragments of any of the above. Immunoglobulin molecules can be of any type, such as IgA, IgD, IgE, IgG and IgM.

An "epitope" refers to the target molecule site that is capable of being recognized by, and bound by, an antibody. For a protein epitope, for example, this may refer to the amino acids (and particularly their side chains) that are bound by the antibody. Overlapping epitopes include at least one to five common amino acid residues. Methods of identifying epitopes of antibodies are known to those skilled in the art and include, for example, those described in Antibodies, A Laboratory Manual, Cold Spring Harbor Laboratory, Ed Harlow and David Lane (1988).

A "complementarity-determining region", or "CDR", refers to amino acid sequences that, together, define the binding affinity and specificity of the Fv region of a native immunoglobulin binding site. There are three CDRs in each of the light and heavy chains of an antibody.

A "framework region", or "FR", refers to amino acid sequences interposed between CDRs.

A "constant region" refers to the portion of an antibody molecule that is consistent for a class of antibodies and is defined by the type of light and heavy chains. For example, a light chain constant region can be of the kappa or lambda chain type and a heavy chain constant region can be of one of the five chain isotypes: alpha, delta, epsilon, gamma or mu. This constant region, in general, can confer effector functions exhibited by the antibodies. Heavy chains of various subclasses (such as the IgG subclass of heavy chains) are mainly responsible for different effector functions.

As used herein, the term "anti-CD45" describes an antibody comprising at least one of the heavy chain CDRs and at least one of the light chain CDRs as described in FIGS. 1 and 2.

A "variable domain sequence" is an amino acid sequence that affects the structure of an immunoglobulin variable domain. This includes all or a part of the amino acid sequence of a naturally occurring variable domain. For example, the sequence may include other alterations that are compatible with formation and maintenance of the protein secondary and tertiary structure.

"Fv" is an antibody fragment that contains a complete antigen-recognition and binding site. This region consists of a dimer of one heavy and one light chain variable domain in tight, non-covalent or covalent association. Three CDRs of each variable domain interact to define an antigen-binding site on the surface of the VH-VL dimer. Collectively, the six CDRs confer antigen-binding specificity to the antibody.

"Immunoreactivity" refers to a measure of the ability of an immunoglobulin to recognize and bind to a specific antigen. In one embodiment, the immunoglobulin binds to its antigen with an affinity ($K_D$) of between $10^{-8}$ M and $10^{-10}$ M.

"Purification", as used herein with respect to an immunoglobulin (or portion thereof), includes, without limitation, the removal of other immunoglobulins and related proteins so that the desired immunoglobulin (or portion thereof) is at least 80% pure, at least 90% pure, at least 95% pure, at least 98% pure, or at least 99% pure.

Unless otherwise defined, all technical and scientific terms used herein have the same meaning as commonly understood by one of ordinary skill in the art to which the present invention belongs. Although methods and materials similar or equivalent to those described herein can be used in the practice or testing described herein, suitable methods and materials are described below. In addition, embodiments of the present invention described with respect to Chothia CDRs may also be implemented using Kabat CDRs.

DETAILED DESCRIPTION OF THE INVENTION

High expression of CD45 antigen is seen on malignant cells associated with most acute lymphoid and myeloid leukemias. A density of approximately 200,000 to 300,000 sites per cell on circulating leukocytes and malignant B cells has been reported. Among normal cells, all the cells of hematopoietic origin, with the exception of mature erythrocytes and platelets, express CD45. It is not found on tissues of non-hematopoietic origin. Therefore, the leukemia-associated CD45 antigen makes it a good target for developing therapeutics, including radio-immunotherapeutics.

The complete amino acid sequence of the anti-CD45 murine immunoglobulin determined by the methods described in Example 2 is shown in FIGS. 3 and 4A. Estimated CDR regions as determined by homology algorithms are shown in FIGS. 1 and 2. The light chain of the anti-CD45-immunoglobulin was found to be a kappa-type chain.

The light chain composed of 218 amino acids contains five cysteine residues. The heavy chain composed of 445 amino acids contains 12 cysteine residues. Both chains fold into immunoglobulin-type domains with expected cysteine pairs well positioned to establish intra-chain disulfide bridges. The hinge region on the heavy chain is composed of three inter-chain disulfide bonds.

The light chain contains 10 tyrosine residues and the heavy chain contains 15 tyrosine residues. Therefore, all together, the anti-CD45 immunoglobulin contains 50 tyrosine residues which could be targeted as radio-iodination sites.

As such, the anti-CD45 immunoglobulin was labeled with radioiodine using the chloramine-T method of radio-iodination as described in Example 3. It was found that an $^{131}$I to immunoglobulin stoichiometry of 20-30 mCi/mg consistently afforded about 90% radio-chemical yield following purification of the radio-iodinated reaction product. Using this stoichiometry ratio, the immunoglobulin can be labeled with high levels of radioactivity (e.g., 300-3,000 mCi, or even 300-5,000 mCi) in a single batch. As detailed in Examples 3, 10 and 11, this radio-iodination process utilizing a 30 mCi/mg murine anti-CD45 immunoglobulin ratio during radio-labeling resulted in product with >90% radio-chemical purity, a radiochemical yield of >90%, and >70% immunoreactivity.

As indicated above, radiolytic damage of $^{131}$I-labelled antibodies has reduced or even precluded their use as therapeutic agents. It is an object of the present invention to employ one or more excipients to stabilize $^{131}$I-labelled anti-CD45.

Radical scavengers are employed here as stabilizers to minimize radiolysis of radiolabeled preparations. These scavengers and stabilizers include, for example, ascorbic acid, gentisic acid, HSA, and polyvinylpyrrolidone (PVP). Ascorbic acid may be included at from 0.1 to 5% (w/v), and may be added post-labeling as a radio-protectant. Gentisic acid may be included at from 0.1 to 0.5% (w/v), or even higher amounts (e.g., 2 to 8%) when included as the sodium salt, and may be added post-labeling. HSA may be added at from 2 to 5% (w/v). Individually and in certain combinations, each excipient may slow radiolysis. In particular, combinations including ascorbic acid at from 0.1 to 5% (w/v), and HSA at from 2 to 5% (w/v), may be advantageous for slowing radiolytic damage of the $^{131}$I-labelled anti-CD45 of the present invention.

PVP is a linear chain water-soluble polymer useful for protecting antibodies against auto-radiolysis. Specifically, the PVP of average molecular weight 6-8 kD and a K-17 value (a designator of its viscosity) is the most useful for these purposes. As such, PVP may be included in the stabilizing formulations disclosed herein at from 0.1% to 6% and even up to 10% (w/v). PVP may also help to prevent aggregation of the protein in a composition.

PVP in combination with a secondary stabilization agent, in particular, ascorbic acid or HAS, is most effective in ameliorating auto-radiolysis of radio-peptides in high radioactive fields (>Ci levels). An effective combination may include, for example, 0.5-5% (w/v) ascorbic acid and 0.5-4% (w/v) PVP, or 0.5-5% (w/v) ascorbic acid, 0.5-5.0% (w/v) HSA, and 0.5-4% (w/v) PVP. Ideally, the PVP and ascorbate combination, or PVP, ascorbate and HSA combination, is added immediately following the radiolabeling of the Ab.

In addition to these agents, a variety of other radio-protective agents can be used, including synthetic thioethers and chromans that provide stability through their free radical scavenging and anti-oxidative properties.

In additional to chemical means of stabilizing a radiolabeled protein, cryopreservation has also been shown to stabilize the labeled preparation in enhancing its shelf life. This was exemplified for three $^{131}$I-labeled-mAbs where a successful technique of cryopreservation at −70° C. for several days was demonstrated to allow for their shipment and administration. The immunoreactivity of these cryoprotected antibodies was fully preserved throughout the course of this investigation (e.g. ~10 days) with minimal radiation decay, as compared to samples stored at 4° C. One caveat to this approach, however, is that an antibody cannot tolerate more than one freeze-thaw cycle.

Thus, another embodiment of the radiolabeling process according to this invention is to employ stability-enhancing excipients as early as possible in the process. For example, excipients such as ascorbic acid (2.5% w/v) may be added alone or in combination with HSA (2% to 4% w/v) to the quenched radio-iodination mixture before the purification of the labeled product, as detailed in Example 3. Excipients may be added using pre-cooled concentrated stock solutions.

Purification of the labeled immunoglobulin over a desalting column may also be carried out in the presence of excipients, such as the 2.5% ascorbic acid or the mixture of 2.5% ascorbic acid and 2 to 4% HSA (all w/v). For example, the excipients may be added in the pre-cooled elution buffer used for purification of the labeled immunoglobulin. The purified product is therefore collected from the desalting column mixed with these stability-enhancing excipients. The purification of a 1,000 mCi aliquot may be performed on a commercially available sterile Sephadex G25 desalting column (GE HiPrep 26/10 desalting column, bed volume 53 mL). Similarly, smaller batches such as <200 mCi labeling can be purified on a commercially available PD10 desalting column (GE PD10 column, bed volume 8.6 mL). The use of pre-sterilized columns provides a convenient method to prepare radiolabeled product doses for human administration. While specific column sizes and matrices have been discussed, columns of other sizes and bed volumes using similar or equivalent matrices may also be used.

The formulation of the product with stability-enhancing excipients is preferentially performed using ascorbic acid, PVP and HSA. As such, the purified radiolabeled product according to this invention may contain ascorbic acid or a mixture of ascorbic acid and HSA. Further, the purified product may be formulated with PVP (for example, at 2% w/v) to help prevent the formation of aggregates (Example 5).

In addition, a cryopreservation approach to minimizing radiation damage to the high radioactivity labeled immunoglobulin may also be used. Prior cryopreservation schemes have used temperatures as low as −70° C. to stabilize an $^{131}$I-labeled antibody. However, surprisingly, it was found that for the radiolabeled immunoglobulin of this invention, cryopreservation at −20° C. gave satisfactory results compatible with targeted stability and shelf life of four days for therapeutic dose formulations and eight days for the dosimetry dose formulations. Furthermore, as described in Examples 8-10, the use of this cryopreservation surprisingly allowed two freeze-thaw cycles while maintaining the integrity and stability of the formulated $^{131}$I-labeled anti-CD45 immunoglobulin of this invention.

Thus, the compositions, stabilizing excipient mixtures and cryopreservation methods of the present invention have been found to provide excellent stabilization of the radio-labelled antibody, providing intact antibodies having immunoreactivity of greater than 70%, greater than 80%, and even greater than 90%.

Various stability-indicating tests performed (Example 7) with the therapeutic and dosimetry dose formulations suggest that, for example, the combination of 2.5% ascorbic acid and 2% PVP (both w/v) as excipients, along with cryopreservation at −20° C., provides good stability of four days and eight days, respectively, for the therapeutic dose and the dosimetry dose formulations. In both instances, the terminal day of storage is at ambient temperature.

Each of the foregoing embodiments that provides excipient-stabilized radio-iodinated anti-CD45 immunoglobulin compositions may find use as a radiotherapeutic agent for treating malignancies of hematopoietic origin.

The following examples of this invention are provided to illustrate its various aspects and by no means are to be viewed as limiting any of the described embodiments. A different combination of these embodiments may be used to achieve similar characteristics of the formulated radio-iodinated immunoglobulins of this invention. For example, the amounts of the excipients used may be varied and the temperature of storage may be changed to 2-8° C. or even room temperature. This may be adaptable to formulations intended for immediate use or use within a short period of 1-2 days.

All publications, patent applications, patents, and other references mentioned herein are incorporated by reference in their entirety. In addition, the materials, methods and examples are illustrative only and not intended to limit the scope of the present invention.

BRIEF DESCRIPTION OF THE SEQUENCES

SEQ ID NO:1 shows the amino acid sequence of the variable domain of the light chain of anti-CD45 murine immunoglobulin BC8.

SEQ ID NO:2 shows the amino acid sequence of the variable domain of the heavy chain of anti-CD45 murine immunoglobulin BC8.

SEQ ID NO:3 shows the amino acid sequence of CDR1 of the light chain of anti-CD45 murine immunoglobulin BC8.

SEQ ID NO:4 shows the amino acid sequence of CDR2 of the light chain of anti-CD45 murine immunoglobulin BC8.

SEQ ID NO:5 shows the amino acid sequence of CDR3 of the light chain of anti-CD45 murine immunoglobulin BC8.

SEQ ID NO:6 shows the amino acid sequence of CDR1 of the heavy chain of anti-CD45 murine immunoglobulin BC8.

SEQ ID NO:7 shows the amino acid sequence of CDR2 of the heavy chain of anti-CD45 murine immunoglobulin BC8.

SEQ ID NO:8 shows the amino acid sequence of CDR3 of the heavy chain of anti-CD45 murine immunoglobulin BC8.

SEQ ID NO:9 shows the nucleotide sequence of the light chain of anti-CD45 murine immunoglobulin BC8.

SEQ ID NO:10 shows the nucleotide sequence of the heavy chain of anti-CD45 murine immunoglobulin BC8.

SEQ ID NO:11 shows the amino acid sequence of N-terminus of the light chain of anti-CD45 murine immunoglobulin BC8.

SEQ ID NO:12 shows the amino acid sequence of N-terminus of the heavy chain of anti-CD45 murine immunoglobulin BC8.

SEQ ID NO:13 shows the predicted amino acid sequence of the light chain of anti-CD45 murine immunoglobulin BC8.

SEQ ID NO:14 shows the predicted amino acid sequence of the heavy chain of anti-CD45 murine immunoglobulin BC8.

SEQ ID NO:15 shows the actual amino acid sequence of the heavy chain of anti-CD45 murine immunoglobulin BC8 as determined by amino-acid sequencing.

EXAMPLES

Example 1: Production of Anti-CD45 Immunoglobulin BC8

The murine anti-CD45 mAb BC8 was prepared from a hybridoma (ATCC No. HB-10507) that was initially developed by fusing mouse myeloma NS1 cells with spleen cells from a BALB/C mouse hyperimmunized with human phytohemagglutinin (PHA)-stimulated mononuclear cells. The original fused cells, after screening for microbial contaminations, were cultured using the JRH-Biosciences EXCell 300 medium supplemented with 1-2% Fetal Bovine Serum (FBS).

The hybridoma cell line was adapted for culture in a serum-free culture medium. Briefly, the cells in culture were slowly and gradually weaned of the serum albumin using the combo medium supplemented with glutamine, cholesterol, insulin and transferrin. The cells were then grown in up to 500 L scale to a density of >1 e6 cells/mL The medium was harvested and processed for the purification of the anti-CD45 antibody using a combination of cation exchange chromatography, Protein-A chromatography, and anion exchange membrane separation. The purified antibody was concentrated by nano-filtration (30 kD cutoff). The concentration of the purified product was measured at 5.2 mg/ml and was stored at 2-8° C.

The purified antibody was characterized by SDS-PAGE, IEF and SEC-HPLC techniques. A single product peak (99.4%) was recorded with SEC-HPLC with about 0.6% aggregates. The non-reducing SDS-PAGE showed the band at 186.55 kD for the antibody. The SDS-PAGE under reduced conditions confirmed the presence of the light and the heavy chains (99.9% together).

Example 2: Sequencing of the Anti-CD45-Immunoglobulin BC8

DNA Sequence: Total RNA was isolated from the hybridoma cells following the technical manual of Trizol® Reagent. The total RNA was analyzed by agarose gel electrophoresis and was reverse transcribed into cDNA using isotype-specific anti-sense primers or universal primers following the technical manual of PrimeScript™ 1st Strand cDNA Synthesis Kit. The antibody fragments of VH, VL, CH and CL were amplified and were separately cloned into a standard cloning vector using standard molecular cloning procedures. Colony PCR screening was performed to identify clones with inserts of correct sizes. More than five single colonies with inserts of correct sizes were sequenced for each antibody fragment. The complete nucleotide sequence of the light and the heavy chains are shown in FIGS. 3 and 4A.

Protein Sequencing by LC-MS/MS: The anti-CD45-immunoglobulin was sequenced using the mass spectrometry peptide mapping approach. The anti-CD45-immunoglobulin was de-glycosylated, reduced and digested with individual enzymes; trypsin, Lys-C and chymotrypsin. The peptide fragments were then analyzed by the LC-coupled mass spectrometry technique using the MS/MS fragmentation analysis approach. In the LC-MS/MS peptide mapping-based sequence, certain isomeric amino acids of the same mass may be mistaken for one another. For example, interpretation between a Leu and Ile can be difficult. The nucleotide-based sequence was used to correct for such ambiguities.

The complete predicted protein sequences of the light and the heavy chain, based on the DNA sequence and standard codon usage, are shown in FIGS. 3 and 4B. Protein sequencing of the heavy and light chains of the BC8 antibody showed that the actual amino acid sequence differs from that predicted by the DNA sequence by only a single amino acid in the heavy chain. The complete actual sequence of the heavy chain, based on this protein sequencing, is shown in FIG. 4A. The codon which codes for the amino acid at position 141 predicts an ASN-141 and not the actual ASP-141 found by protein sequencing.

This type of post-translational modification, deamination, may depend on the cellular environment and, in some cases, has been postulated to be related to protein age (e.g., may provide a signal for protein degradation). The fact that other deaminated amino acids were not identified, however, may be indicative of an important and specific role for ASP-141. At the very least, ASP-141 may be in an exposed or accessible region on the folded protein. That is, ASN-141 may be solvent accessible and reside within a conformationally flexible region of the antibody. The effect of deamination on the biological activity of the BC8 antibody may be determined from the results of human clinical trials.

Example 3: Radio-Iodination of Anti-CD45 Immunoglobulin BC8 and its Purification in the Presence of Ascorbic Acid One mg of anti-CD45 immunoglobulin was labeled with 20 to 30 mCi of $^{131}$I-Na (30 mCi) in the presence of chloramine-T (23 micrograms) in PBS buffer (pH 7.2). The reaction was quenched with the addition of aqueous sodium thiosulfate (69 micrograms) and diluted with cold NaI (1 mg). Immediately following, a concentrated ascorbic acid solution made in 50 mM PBS (pH 7) was added to achieve 2.5% (w/v) ascorbic acid strength in the quenched reaction mixture. Labeling reactions up to 3,000 mCi per batch were successfully performed using this method.

The labeled product was purified by gel filtration on a sterile, pre-packed commercially available Sephadex G25 column (GE HiPrep 26/10 column, bed volume 53 mL) using PBS (50 mM, pH 7) mobile phase supplemented with 2.5% (w/v) ascorbic acid to stabilize the radiolabeled product. Up to 1,000 mCi reaction volume was purified on a single column. The product was collected in the five to 35 mL elution volume from the column.

The radio-iodinated reaction batches of <200 mCi could be purified in a similar fashion on a smaller desalting column (GE PD10 column, bed volume 8.6 mL).

Example 4: Radio-Iodination of Anti-CD45 Immunoglobulin BC8 and its Purification in the Presence of Ascorbic Acid and HSA The labeling and purification were performed essentially as described in Example 3, except that 2% or 4% (w/v) HSA was also added along with 2.5% (w/v) ascorbic acid to the quenched reaction as well as in the elution buffer during the purification process.

Example 5: Formulation of $^{131}$I-Anti-CD45 Immunoglobulin BC8 to Stabilize it Against Auto-Radiolysis Aliquots of the purified product were formulated at once for stability test studies under various storage conditions and durations. The storage test conditions included −20° C., 2-8° C., room temperature and a combination thereof. The duration of storage was three days to 15 days, followed by one additional terminal day at room temperature. The −20° C. conditions were intended to stabilize the formulated product against auto-radiolysis. The terminal 24 hr room temperature condition was to test for stability of the product during its administration to human subjects.

The purified $^{131}$I-anti-CD45-immunoglobulin product contained 2.5% (w/w) ascorbic acid (as in Example 3) and additionally 2 or 4% (w/v) HSA (as in Example 4). In either case, the product was further formulated by supplementing it with 2 or 4% (w/v) PVP. The PVP was added for its influence in preventing the formation of protein aggregates. In this invention, $^{125}$I and $^{123}$I are also envisioned for use in radiolabeling Anti-CD45 Immunoglobulin (e.g., BC8).

All of the formulated products were assayed for stability and immunoreactivity following the above mentioned stability test paradigms.

Example 6: Stabilized Formulations of $^{131}$I-Anti-CD45 Immunoglobulin BC8 for Dosimetry and Therapeutic Applications The purified product was formulated at once into unit doses for dosimetry and therapeutic applications. Appropriate aliquots (mCi) of the purified $^{131}$I-anti-CD45 immunoglobulin were formulated into single doses, each having a 45 mL dose volume. The radioactivity drawn in the aliquots was calculated for the desired calibration time (CT) of three days for the therapeutic dose and seven days for the dosimetry dose. A single lot of purified $^{131}$I-BC8 was used to make a combination of single unit dosimetry and therapeutic doses.

To make a dosimetry dose formulation, a 6 to 12 mCi aliquot (for CT of seven days) was formulated to a 50 mL dose volume, by combining it with appropriate amounts of "cold" (i.e., unlabeled) anti-CD45 immunoglobulin (35 mg final amount of the combined labeled and unlabeled antibody fractions in 45 mL dose volume for a 70 kg subject), 2.5% (w/v) ascorbic acid and 2% (w/v) PVP. A 45 mL portion was filled in the dose vial. The remaining 5 mL was filled in a vial designated for QC tests. After formulation, the doses can be stored at −20° C. for up to seven days for use within this time period. For human administration, a dose received at −20° C. could be allowed to stand at room temperature for one to two hours to thaw it. It may then be infused into the patient within the next 22 hours.

The therapeutic dose formulations were made patient-specific both in terms of dose-associated radioactivity and the amount of the anti-CD45 immunoglobulin. The radioactivity dose amount as prescribed by the clinical investigator was formulated by matching it with the calculated amount of total anti-CD45 immunoglobulin (cold anti-CD45 immunoglobulin plus $^{131}$I-radiolabeled anti-CD45 immunoglobulin fraction) adjusted for the weight of the patient to deliver 0.5 mg/kg BC8 antibody dose in a 45 mL dose volume. A therapeutic dose formulation was also adjusted to a final 2.5% (w/v) ascorbic acid and 2% (w/v) PVP. Using these parameters, a 50 mL volume of the therapeutic dose was made, of which 45 mL are transferred to a dose vial. The remaining 5 mL of the formulation is placed in a vial designated for QC tests. The formulated dose could be stored at −20° C. for up to three days for administering within this period. A dose received by the clinical site at −20° C. could be allowed to stand at room temperature for one to two hours to thaw it. It may then be infused into the patient within next 22 hours.

Example 7: Analytical Methods for Testing the Stability of $^{131}$I-Anti-CD45-Immunoglobulin BC8

The radiochemical purity and immune-reactivity of the $^{131}$I-labeled BC8 are two important measurable analytical parameters that determine its suitability for clinical use as a dosimetry agent and a therapeutic agent. Various analytical methods employed to establish these requirements are described herein.

(A) Radiochemical Incorporation by Instant Thin-Layer Chromatography (iTLC).

Silica-impregnated iTLC strips of dimension 10.5×1.0 cm (Gelman Sciences Inc., Ann Arbor, Mich.; or Varian ITLC-SG; SG10001) were employed for this test. Each strip was marked with pencil lines at 1.5, 6.0 and 6.5 cm from one edge. The strip was spotted on the 1.5-cm line with about 25-50 μCi of the $^{131}$I-BC8 preparation (generally, 1-5 μL). The strip was then set in a 15-mL plastic centrifuge tube containing about 2 mL of normal saline (or PBS buffer, or sodium acetate buffer) to serve as the mobile phase. The iTLC strip was developed until the mobile saline phase had reached the top of the strip. The strip was taken out of the tube and cut at the 6.0- and 6.5-cm lines. The activities of the top, middle and bottom sections were measured in a dose calibrator. The radiochemical incorporation of $^{131}$I to the immunoglobulin protein was calculated as the activity of the bottom section divided by the total activity in all three sections. The acceptance criterion was RCP ≥90%. Significant (≥5%) activity in the middle section would be indicative of streaking and require a re-test.

$$\text{Radiochemical incorporation (\%)} = \frac{\text{(Bottom counts)}}{\text{(Bottom + Middle + Top count)}}$$

For the purified $^{131}$I-anti-CD45-immunoglobulin preparations, this method showed 98-100% of the radioiodine in the immunoglobulin with an almost immeasurable amount of radioactivity in the top half of the iTLC strip. The free $^{131}$I, if present, is carried to the top of the strip by the mobile phase. This test, therefore, routinely established that during the purification of the $^{131}$I-anti-CD45 immunoglobulin by desalting chromatography immediately following the radioiodination reaction, the free iodine was effectively removed from the labeled product.

(B) Radiochemical Purity Test (RCP) by Size Exclusive Chromatography-High Pressure Liquid Chromatography (SEC-HPLC).

The HPLC-SEC assay was performed using a YMC-pack-Diol 200 column, using a 50 mM phosphate, 150 mM NaCl mobile phase at pH 7.2 and a flow rate of 0.5 mL/min. The column was first rinsed with 10 mM phosphate, pH 7.0 for at least 60 minutes. It was then equilibrated with the mobile phase for another 60 minutes before injection of the sample. Samples were run for 45 minutes, with blanks (water) injected between each sample to ensure there was no overlap of peaks from one sample to the next. A reference standard was also tested to compare the main peak elution time.

Figures 9A, 9B:
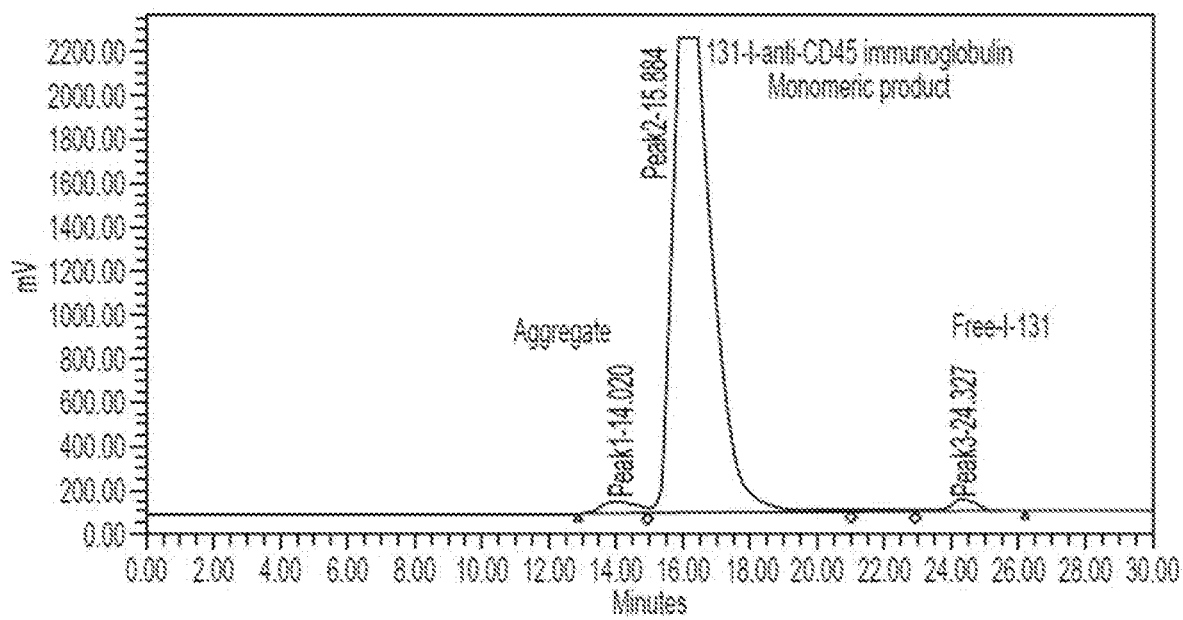
FIGS. 9A and 9B show a typical radio-elution SEC-HPLC profile of a purified $^{131}$I-anti-CD45-immunoglobulin (FIG. 9A) and the area percent of each eluent from peak integration (FIG. 9B).

The SEC using this column allows for the separation of the $^{131}$I-anti CD45 immunoglobulin protein into the product (monomeric) and aggregated fractions, in addition to the free unconjugated radio-iodine and other smaller protein degradation fragments. The radiochemical purity of $^{131}$I-anti-CD45 immunoglobulin using HPLC-SEC is obtained using an in-line flow gamma radioactivity detector. A typical profile and integration results are shown in FIGS. 9A and 9B.

The data for a typical run were obtained as the % radioactivity associated with the $^{131}$I-anti CD45-immunoglobulin product (monomer), the high molecular weight species or aggregated protein, and the free-$^{131}$I. For the purified $^{131}$I-anti CD45-immunoglobulin preparations, this method consistently showed (a) >95% monomer peak corresponding to the desired labeled product; (b) <5% aggregates; and (c) <5% of low molecular-weight impurities, including the free $^{131}$I. A comparison of these three critical quality attributes among various formulations and stability conditions was made to understand the effectiveness of a formulation and its stability over a period of time and temperature conditions.

(C) Immunoreactivity Assays.

In these assays, Raji, Ramos, or CytoTrol (Beckman Coulter) cells expressing cell surface CD45 antigen were used to determine specific binding of $^{131}$I-anti-CD45-immunoglobulin to CD45 antigen-positive cells. The CytoTrol cells were lyophilized human lymphocytes isolated from peripheral blood that exhibit CD45 surface antigen and were preferred due to their commercial availability (Beckman Coulter) and consistency.

(i) Direct binding assay: An aliquot of the $^{131}$I-anti-CD45 immunoglobulin was diluted to 30 ng/mL. A 2-mL microcentrifuge vial was charged with 100 μL of cells (2.5×10$^7$ CytoTrol cells) and 150 μL of the diluted $^{131}$I-anti-CD45 immunoglobulin (4.5 ng protein). For the measurement of total activity termed "Applied Total", another vial was charged with only the $^{131}$I-BC8 solution (150 The assay was performed in triplicate. The cell-protein mixtures were incubated on a rocker at 37° C. for one hour, and then centrifuged at 2,000 rpm for two minutes. A specific volume of the supernatant from each vial (188 μL) was transferred by pipette to empty micro-centrifuge vials. The activity in each vial of supernatant (as well as in the "Applied Total" vials) was measured with a NaI well counter (Capintec), counting each vial for one minute. The % binding of $^{131}$I-BC8 to CytoTrol cells was then calculated as:

$$\text{Binding (\%)} = \frac{\text{(Applied Total activity)} - \left(\frac{4}{3}\right)\text{(supernatamt activity)}}{\text{(Applied Total activity)}}$$

A >70% specific binding was considered an acceptable level of immunoreactivity for the $^{131}$I-radiolabeled product.

(ii) ELISA competition assay: A cell basis ELISA competition assay was also used to measure $^{131}$I-anti-CD45-immunoglobulin BC8 binding affinity to CytoTrol cells. In this assay, various concentrations of $^{131}$I-anti-CD45-immunoglobulin were made to compete with the binding of a fixed concentration of CD45-FITC antibody to the CytoTrol cells. The CD45-FITC antibody is a fluorescein isothiocyanate (FITC)-labeled monoclonal antibody that reacts with all isoforms of human CD45. The increasing concentrations of $^{131}$I-anti-CD45-immunoglobulin displaced the CD45-FITC bound to CytoTrol cells. The binding activity was then measured in terms of fluorescence of CD45-FITC bound on CytoTrol cells. The immunoreactivity of $^{131}$I-anti-CD45-immunoglobulin was defined as the concentration of $^{131}$I-anti-CD45-immunoglobulin at which ≥80% cell binding of CD45-FITC antibody to CytoTrol cells was displaced.

(iii) Flow Cytometry Assay: A Flow Cytometry assay can also be used to evaluate the immunoreactivity of the $^{131}$I-anti-CD45-immunoglobulin formulations. The specific binding to the CD45 cell surface antigen (on CytoTrol or Raji Cells) was measured in terms of an arithmetic mean, geometric mean, or median fluorescence intensity (MFI). The MFI should demonstrate radiolabeled anti-CD45-immunoglobulin binding: >50% of the positive control antibody with known binding ability. The positive control antibody in this assay could be the native (unlabeled) anti CD45-immunoglobulin.

Example 8: Stability Studies on a 100 mCi $^{131}$I-Anti-CD45-Immunoglobulin Formulated with (w/v) 2.5% Ascorbic Acid, 4% HSA and 2% PVP A 100 mCi aliquot of the initial labeled product containing 2.5% ascorbic acid and 4% HSA (prepared by the methods of Examples 4 and 5) was stored frozen at −20° C. for three days, thawed and assayed according to methods of Example 7. It was then formulated to include 2% PVP and stored at −20° C. for three days, then thawed, assayed and left at ambient temperature for one day. Day 7 assays were also performed for comparisons.

The assay results shown in FIGS. 5A-5D describe a very high stability of the labeled and formulated product and resistance to degradation by two freeze/thaw cycles during the entire stability testing process. The monomeric protein bound activity at all the test points over the entire seven-day period, which include the terminal day 7 at room temperature, were well over 90% with acceptable immunoreactivity of >80%. The aggregates (HMWS) and the Free-I (LMWS) were also well contained; <3% and <4.5% respectively. Considering the half-life of $^{131}$I (8.02 days), these 7-day stability results are remarkable for the exemplary excipient-stabilized formulation.

Example 9: Stability Testing of Three Therapeutic Dose Formulations Using (w/v) 2.5% Ascorbic Acid and 2% PVP for Over a 4-Day Period

TABLE 1

Summary of key stability parameters of therapeutic dose formulations studied

| Labeling Batch | Therapeutic Formulation | Formulation excipient | | | iTLC | | | IR (% Cell Binding) | | | SEC-HPLC | | | |
|---|---|---|---|---|---|---|---|---|---|---|---|---|---|---|
| | | AA % | PVP % | HSA % | T = 0 | T = 0-3 day at −20 C. | T = day 4 at RT | T = 0 | T = 0-3 day at −20 C. | T = day 4 at RT | | T = 0 | T = 0-3 day at −20 C. | T = day 4 at RT |
| 1,000 mCi Run-3 | 895 mCi formulation | 2.5 | 2 | — | 99.64 | 98.93 | 97.99 | 83.3 | 79.1 | 78.8 | Prod. Free Aggr. | 96.47 1.25 2.28 | 94.27 3.38 2.35 | 92.83 5.05 2.13 |
| 3,000 mCi Run-4 | 1,182 mCi - Th-A formulation | 2.5 | 2 | — | 99.60 | 98.90 | 98.80 | 80.9 | 80.8 | 75.9 | Prod. Free Aggr. | 96.69 1.14 2.18 | 92.83 3.89 3.28 | 92.47 5.59 1.94 |
| 3,000 mCi Run-4 | 1,133 mCi Th-B: formulation | 2.5 | 2 | 2% | 99.59 | 98.30 | 98.30 | 83.2 | 79.9 | 76.2 | Prod. Free Aggr. | 96.86 1.07 2.06 | 93.94 3.72 2.34 | 91.21 6.21 2.57 |

AA—acetic acid;
PVP—polyvinylpyrrolidone;
HSA—human serum albumin

Figure 6A:
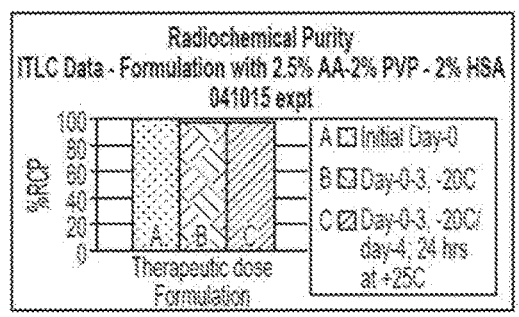
FIGS. 6A-6C provide bar graphs of stability test data of a 1,100 mCi therapeutic dose formulation of $^{131}$I-anti-CD45 immunoglobulin over a total period of four days which included a freeze thaw cycle. SEC-HPLC results showing % product (FIG. 6A), % free-$^{131}$I and % fraction of aggregates (FIG. 6C), and immunoreactivity results (FIG. 6B) are shown for various time points. The time points of this stability study and the formulation excipient composition were as follows. The radiolabeled anti-CD45 antibody initially formulated during the purification process contained 2.5% (w/v) ascorbic acid, and was formulated with 2% (w/v) PVP and tested on day-0, and following its storage for 0-3 days at −20° C. On day-3, after thawing, the radiolabeled anti-CD45 antibody was stored at room temperature, during which stability was tested at 8 and 24 hours (storage time at room temperature).
Figure 6B:
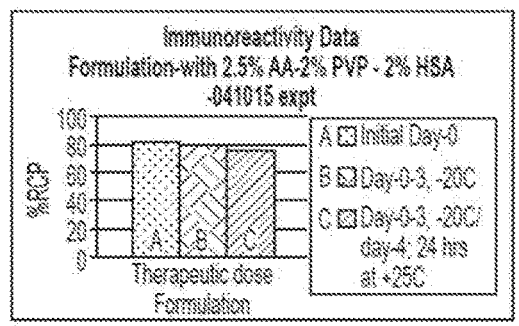
Figure 6C:
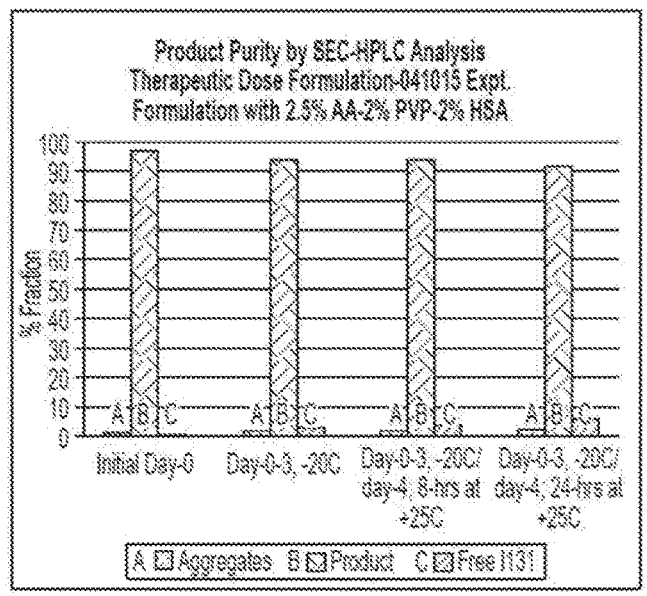

Aliquots (895, 1,133 and 1,182 mCi) from 1,000 to 3,000 scale labeling runs performed according to the methods of Example 3, or Examples 3 and 4 combined, were formulated with 2% (w/v) PVP. Table 1 details these individual therapeutic dose formulations and stability testing results using a protocol of 3-day storage at −20° C. followed by an additional day at room temperature. The stability-indicating assays were performed according the methods of Example 7. All the test results at the end of day 4 showed >90% monomeric product fraction with a maximum of 6.21% of Free-I and 3.3% aggregates, signifying high stability of the product. The immunoreactivity of >75% at the day 4 time point was also excellent. FIGS. 6A-6C show histograms of the 1,133 mCi therapeutic formation of this set.

Example 10: Stability Testing of Seven Dosimetry Dose Formulations Using (w/v) 2.5% Ascorbic Acid and 2% PVP for Up to an 8-Day Period

TABLE 2

Summary of key stability parameters of dosimetry dose formulations studied

| Scale of Labeling batch | Dosimetry Formulation | Formulation excipient | | | iTLC | | | IR (% Cell Binding) | | | SEC-HPLC | | | |
|---|---|---|---|---|---|---|---|---|---|---|---|---|---|---|
| | | AA % | PVP % | HSA % | T = 0 | T = 0-7 day at −20 C. | T = day 8 at RT | T = 0 | T = 0-7 day at −20 C. | T = day 8 at RT | | T = 0 | T = 0-7 day at −20 C. | T = day 8 at RT |
| 300 mCi | A - 12 mCi formulation | 2.5 | 2 | 4 | 99.60 | 99.98 | 98.39 | 85.3 | 80.1 | 77.9 | Prod. Free Aggr. | 95.50 2.70 2.70 | 95.99 1.85 2.16 | 96.2 2.11 1.69 |

TABLE 2-continued

Summary of key stability parameters of dosimetry dose formulations studied

| Scale of Labeling batch | Dosimetry Formulation | Formulation excipient | | | iTLC | | | IR (% Cell Binding) | | | SEC-HPLC | | | |
|---|---|---|---|---|---|---|---|---|---|---|---|---|---|---|
| | | AA % | PVP % | HSA % | T = 0 | T = 0-7 day at −20 C. | T = day 8 at RT | T = 0 | T = 0-7 day at −20 C. | T = day 8 at RT | | T = 0 | T = 0-7 day at −20 C. | T = day 8 at RT |
| 300 mCi | B - 18 mCi formulation | 2.5 | 2 | 4 | 99.60 | 99.78 | 98.53 | 85.3 | 80.4 | 77.2 | Prod. Free Aggr. | 97.50 1.06 1.44 | 95.65 2.07 2.28 | 95.61 2.28 2.11 |
| 300 mCi | 12 mCi formulation | 2.5 | 2 | 4 | 96.85 | 97.26 | 96.47 | 77.9 | 79.9 | 76.1 | Prod. Free Aggr. | 96.85 1.32 1.82 | 97.26 1.29 1.45 | 96.47 1.99 1.54 |
| 1,000 mCi | A - 11.56 mCi formulation | 2.5 | 2 | — | 99.75 | 98.91 (d = 3, −20 C.) | 98.83 (d = 4 RT) | 83.8 | 80.9 (d 3) | 77.3 (d 4) | Prod. Free Aggr. | 96.88 0.92 2.20 | 96.39 (d 3) 1.25 (d 3) 2.36 (d 3) | 96.54 (d 4) 1.81 (d 4) 1.65 (d 4) |
| 1,000 mCi | B - 11.25 mCi formulation | 2.5 | 2 | — | 99.75 | 96.08 | na | 83.8 | 78.7 | na | Prod. Free Aggr. | 96.88 0.92 2.20 | 96.11 1.43 2.47 | Na Na Na |
| 3,000 mCi | Ds-A - 15.03 mCi formulation | 2.5 | 2 | — | 98.97 | 98.80 (d 3) | 98.3 (d 4) | 80.4 | 81.2 (d 3) | 80.7 (d 4) | Prod. Free Aggr. | 96.68 1.25 2.08 | 95.38 (d 3) 1.58 (d 3) 2.41 (d 3) | 96.6 (d 4) 1.33 (d 4) 2.07 (d 4) |
| 3,000 mCi | Ds-B - 13.78 mCi formulation | 2.5 | 2 | — | 98.97 | 97.72 | 97.12 | 80.4 | 78.4 (d 6) | 71.5 (d 7) | Prod. Free Aggr. | 96.68 1.25 2.08 | 96.88 (d 6) 1.85 (d 6) 1.26 (d 6) | 96.76 (d 7) 1.41 (d 7) 1.82 (d 7) |

RT is room temperature.
The d 3, d 4, d 6 and d 7 stands for day 3 to day 7

Figure 7A:
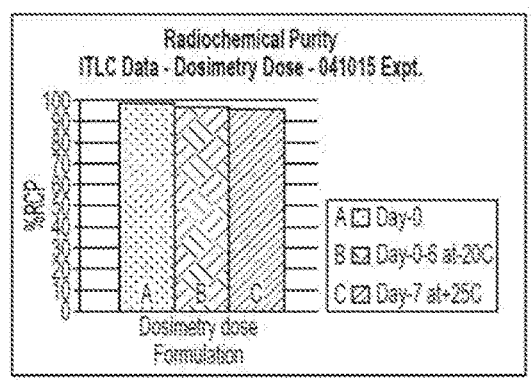
FIGS. 7A-7C provide bar graphs of the stability test data of a 13 mCi dosimetry dose formulation of $^{131}$I-anti-CD45 immunoglobulin over a total period of seven days which included a freeze thaw cycle. SEC-HPLC results showing % product (FIG. 7A), % free-$^{131}$I and % fraction of aggregates (FIG. 7C), and immunoreactivity results (FIG. 6B) are shown for various time points. The time points of this stability study and the formulation excipient composition were as follows. The radiolabeled anti-CD45 antibody initially formulated during the purification process contained 2.5% (w/v) ascorbic acid and was further formulated with 2% (w/v) PVP and tested on day-0, and following its storage for 0-6 days at −20° C. On day-6 the formulated product was thawed and stored at room temperature for an additional 24 hours after which the stability tests were repeated.
Figure 7B:
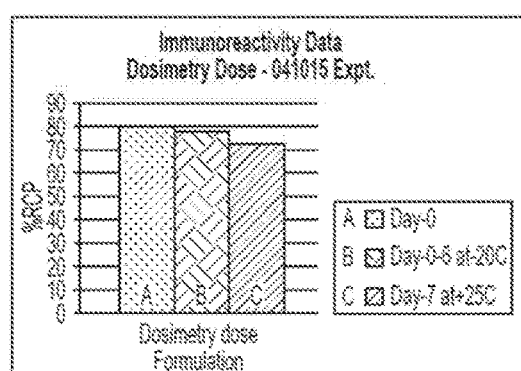
Figure 7C:
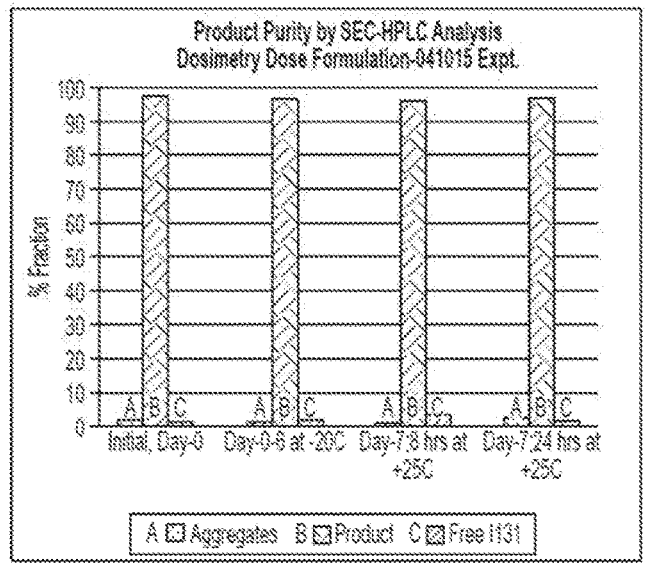
Figure 8A:
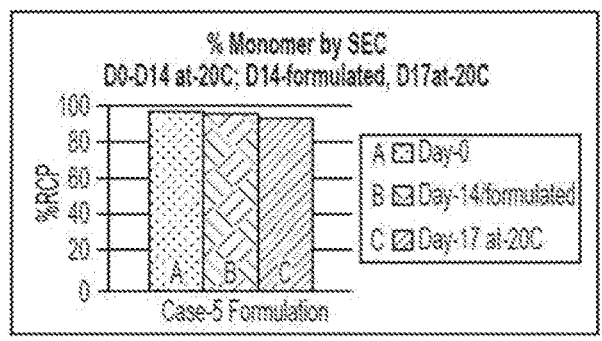
FIGS. 8A-8D provide bar graphs of the stability test data of a 150 mCi dose of $^{131}$I-anti-CD45 immunoglobulin over a total period of 17 days which included two freeze thaw cycles. SEC-HPLC results showing % product (FIG. 8A), % free-$^{131}$I (FIG. 8D) and % fraction of aggregates (FIG. 8B), and immunoreactivity results (FIG. 8C) are shown for various time points. The time points of this stability study and the formulation excipient composition were as follows. The radiolabeled anti-CD45 antibody initially formulated during the purification process contained 2.5% ascorbic acid and 4% HSA (both w/v) was tested on day 0, and following its storage for 0-14 days at −20° C. On day-14 after thawing, it was then further formulated with 2% (w/v) PVP, tested and once again stored at −20° C. for three additional days. Both the stability tests were performed on day-17 after thawing. It is noteworthy that the 17-day period is almost close to two half-lives of the $^{131}$I isotope (half-life 8.02 days).
Figure 8C:
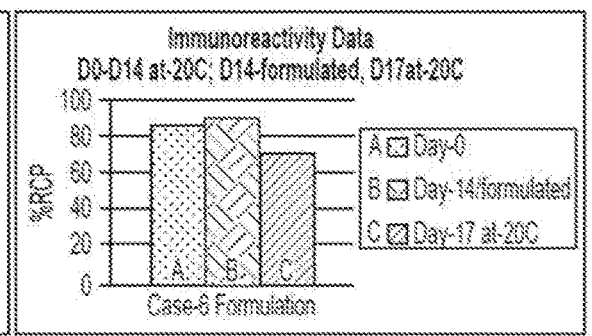
Figure 8B:
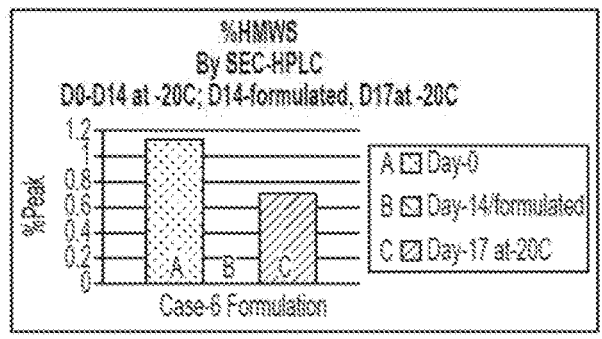
Figure 8D:
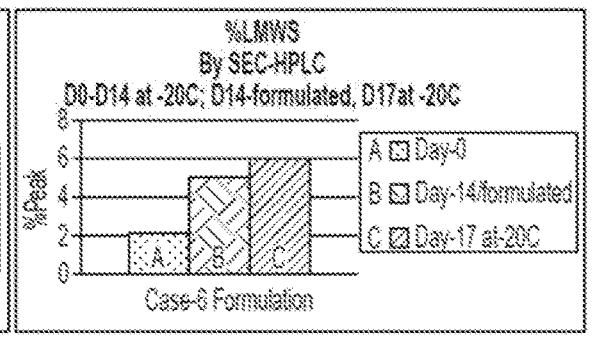

Seven 11 to 18 mCi aliquots from 300 to 3,000 scale labeling runs performed according to the methods of Example 3 or Example 3 and 4 combined were formulated with 2% (w/v) PVP. Table 2 describes these individual dosimetry dose formulations and stability testing results using a protocol of 3- or 7-day storage at −20° C. followed by an additional day at room temperature. The stability-indicating assays were performed according the methods of Example 7. All test results at the end of day 4 or day 8 showed >95% monomeric product fraction with a maximum of 2.8% of Free-I and 2.7% aggregates, signifying high stability of the formulated product. The immunoreactivity of >75% at the day 4 time point and >70% at day 8 time point was also well within acceptable range. FIGS. 7A-7C show histograms of the 13.78 mCi dosimetry dose formation of this set as a representative example.

Example 11: Stability Studies on a 150 mCi $^{131}$I-Anti-CD45-Immunoglobulin Formulated with (w/v) 2.5% Ascorbic Acid and 4% HSA as Well as 2.5% Ascorbic Acid, 4% HSA and 2% PVP A 150 mCi aliquot of the initial labeled product containing 2.5% ascorbic acid and 4% HSA (prepared using the methods of Examples 3 and 4) was stored frozen at −20° C. for 14 days. It was thawed, assayed using methods of Example 7, and further formulated with the inclusion of 2% PVP. This fully formulated product was assayed and again deposited at −20° C. for three additional days. It was finally thawed on day 17 and assayed. This entire stability study included two freeze-thaw cycles, and the combined 17-day stability period is more than two half lives of the $^{131}$I isotope.

The results shown in FIGS. 8A-8D underscore the stability of the fully formulated sample for over 17 days (more than double the ~eight-day half-life of $^{131}$I). The monomeric protein-bound activity at all the test points over the entire 17-day period was >90%, with an immunoreactivity of >70%. The aggregate fraction (HMWS) and the Free-I (LMWS) were also well contained at <1% and <6%, respectively. The immunoreactivity of the sample frozen for 14 days was recorded to be >85%. These assay results for long-term storage of the labeled product (total 17 days) indicate good overall stability of the labeled product and its resilience to prolonged freezing for two weeks followed by two thawing cycles.

Example 12: Additional Embodiments of $^{131}$I-BC8 Formulations

In one embodiment, each $^{131}$I-BC8 dosimetric dose contains a volume of 45±1 mL with 31.5-38.5 mg of BC8, composed of 131I-labeled BC8 and unlabeled BC8, in a solution of 50 mM sodium phosphate buffered saline (0.9%) (pH 7.0) containing 25 mg/mL ascorbic acid, and 20 mg/mL PVP. The dosimetric dose contains 10 (or 10-15) mCi of $^{131}$I-BC8, and is intended for complete infusion during i.v. administration.

In another embodiment, each $^{131}$I-BC8 therapeutic dose contains a volume of 45±1 mL with 6.66-45.0 mg of BC8, composed of $^{131}$I-labeled BC8 and unlabeled BC8, in a solution of 50 mM sodium phosphate buffered saline (0.9%) (pH 7.0) containing 25 mg/mL ascorbic acid, and 20 mg/mL PVP. The therapeutic dose contains 200-1,350 mCi of $^{131}$I-BC8, depending on patient-specific needs, and is intended for complete infusion during i.v. administration. The therapeutic dose does not exceed a ratio of 30:1 of mCi to mg of antibody.

The therapeutic dose activity level is calculated based on gamma camera images following the dosimetric administration using Medical Internal Radiation Dose (MIRD) method and Organ Level Internal Dose Assessment (OLINDA) software to calculate absorbed dose per unit of administered activity to project levels not exceeding 24Gy of activity to any normal organ and 48Gy of activity to the bone marrow.

In one embodiment of these $^{131}$I-BC8 formulations (i.e., doses), the formulations are prepared and stored in the form of batches, whereby each batch is ultimately divided into individual doses. So, for example, one batch might contain between 1-2 Ci, 1-3 Ci, 2-3 Ci, 1-4 Ci, 2-4 Ci, 1-5 Ci, 2-5 Ci, 3-5 Ci, 4-5 Ci, 1-10 Ci, 2-10 Ci, 3-10 Ci or 5-10 Ci. In a 3 Ci batch, for example, the molar ratio of $^{131}$I to antibody is 0.28, the molar ratio of ascorbate to $^{131}$I is 53.83, and the molar ratio of ascorbate to antibody is 415.64. In a 2 Ci batch, for example, the molar ratio of $^{131}$I to antibody is 0.18, the molar ratio of ascorbate to $^{131}$I is 80.74, and the molar ratio of ascorbate to antibody is 277.09. By way of further example, in a 3 Ci batch, the molar ratio of ascorbate to $^{131}$I is below 60, below 55, below 50, below 45, below 40, below 35, below 30, below 25 or below 20; and/or the molar ratio of ascorbate to antibody is below 500, below 450, below 400, below 350, below 300, below 250 or below 200.

REFERENCES

U.S. Pat. Nos. 5,093,105; 5,306,482; 5,384,113; 5,393,512; 5,961,955; 6,066,309; 6,315,979; 6,338,835; and 7,825,222.

U.S. Patent Application Publication No. 2009/0005595.

Bartolini, P., De Assiss, L. M., Fonseca, M. L. C. Q. (1981) Radioiodination of human growth hormone with characterization and minimization of the commonly defined "damage products", Clin. Chim. Acta, 110:177-185.

Beverley, P. C., et al. (1988) *Phenotypic diversity of the CD45 antigen and its relationship to function*, Immunol. Suppl. 1:3-5.

Garrison, W. M. (1987) Chem. Rev. 87(2):381-398.

Gopal, A. K., et al. (2009) $^{131}$*I-anti-CD45 radioimmundtherapy effectively targets and treats T-cell non-Hodgkin lymphoma*, Blood 113(23): 5905-5910.

Kishore, R., et al. (1986) *Autoradiolysis of iodinated monoclonal antibody preparations*. Int. J. of Radial. Appl. Instrum. Part B, Nucl. Med. and Biot. 4:457-459.

Lin, Y., et. al. (2006) *A genetically engineered anti-CD45 single-chain antibody-streptavidin fusion protein for pretargeted radioimmunotherapy of hematologic malignancies*, Cancer Res. 66:3884-3892.

Matthews, D. C., et al. (1991) *Radiolabeled anti-CD45 monoclonal antibodies target lymphohematopoietic tissue in the macaque*, Blood 78(7):1864-1874.

Matthews, D. C., et al. (1995) *Development of a marrow transplant regimen for acute leukemia using targeted hematopoietic irradiation delivered by $^{131}$I-labeled anti-CD45 antibody, combined with cyclophosphamide and total body irradiation*, Blood 85(4); 1122-1131.

Matthews, D. C., et al. (1999) *Phase I study of (131) I-anti-CD45 antibody plus cyclophosphamide and total body irradiation for advanced acute leukemia and myelodysplastic syndrome*, Blood 94(4): 1237-1247.

Streuli, M. F., et al. (1987) *Differential usage of three exons generates at least five different mRNAs encoding human leukocyte common antigens*, J. Exp. Med. 166(5):1548-1566.

Terry, L. A., et al. (1988) *The monoclonal antibody, UCHL1, recognizes a 180,000 MW component of the human leucocyte-common antigen*, CD45, Immunol. 64(2):331-336.

Thomas, M. L., Lefrancois, L. (1988) *Differential expression of the leukocyte-common antigen family*, Immunol. Today 9:320-326.

Wahl, R. L., Wissing, J., del Rosario, R., and Zasadny, R. K., (1990) *Inhibition of autoradiolysis of radiolabeled monoclonal antibodies by cryopreservation*, J. Nucl. Med. 31:84-89.

What is claimed is:

1. An aqueous composition comprising:
    a radiolabeled monoclonal antibody against CD45, wherein the radiolabeled antibody comprises a heavy chain having complementarity determining regions with amino acid sequences as set forth in SEQ ID NOS:6-8, and an aspartic acid at position 141,
    a light chain having complementarity determining regions with amino acid sequences as set forth in SEQ ID NOS:3-5, and
    a pharmaceutically acceptable carrier that includes 0.5% to 5.0% (w/v) of ascorbic acid and 0.5% to 4.0% (w/v) of PVP.

2. The composition of claim 1, wherein the radiolabeled antibody comprises a radiolabel selected from $^{131}$I, $^{90}$Y, $^{177}$Lu, $^{186}$Re, or $^{188}$e.

3. The composition of claim 1, further comprising 0.5% to 5.0% (w/v) of HSA.

4. The composition of claim 1, wherein the heavy chain of the radiolabeled antibody comprises an N-terminal region with the amino acid sequence as set forth in SEQ ID NO:12.

5. The composition of claim 1, wherein the heavy chain of the radiolabeled antibody comprises the amino acid sequence as set forth in SEQ ID NO:14.

6. The composition of claim 1, wherein the composition further comprises non-radiolabeled antibody against CD45, wherein the non-radiolabeled antibody against CD45 is the same as the radiolabeled antibody against CD45.

7. An aqueous composition comprising:
a radiolabeled antibody against CD45, and
0.5% to 5.0% (w/v) ascorbic acid and 0.5% to 5.0% (w/v) polyvinylpyrrolidone (PVP), wherein the radiolabeled antibody comprises:
a heavy chain comprising complementarity determining regions having the amino acid sequences as set forth in SEQ ID NO: 6, SEQ ID NO:7, and SEQ ID NO:8, and
a light chain comprising complementarity determining regions having the amino acid sequences as set forth in SEQ ID NO: 3, SEQ ID NO:4, and SEQ ID NO:5.

8. The composition of claim 7, wherein the radiolabeled antibody comprises a radiolabel selected from $^{131}I$, $^{90}Y$, $^{177}Lu$, $^{186}Re$, or $^{188}e$.

* * * * *

SEQUENCE LISTING

```
<160> NUMBER OF SEQ ID NOS: 15

<210> SEQ ID NO 1
<211> LENGTH: 111
<212> TYPE: PRT
<213> ORGANISM: murine

<400> SEQUENCE: 1

Asp Ile Ala Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
```

-continued

```
                100                 105                 110
```

<210> SEQ ID NO 2
<211> LENGTH: 123
<212> TYPE: PRT
<213> ORGANISM: murine

<400> SEQUENCE: 2

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser Ser Ala Lys
        115                 120
```

<210> SEQ ID NO 3
<211> LENGTH: 15
<212> TYPE: PRT
<213> ORGANISM: murine

<400> SEQUENCE: 3

```
Arg Ala Ser Lys Ser Val Ser Thr Ser Gly Tyr Ser Tyr Leu His
1               5                   10                  15
```

<210> SEQ ID NO 4
<211> LENGTH: 7
<212> TYPE: PRT
<213> ORGANISM: murine

<400> SEQUENCE: 4

```
Leu Ala Ser Asn Leu Glu Ser
1               5
```

<210> SEQ ID NO 5
<211> LENGTH: 9
<212> TYPE: PRT
<213> ORGANISM: murine

<400> SEQUENCE: 5

```
Gln His Ser Arg Glu Leu Pro Phe Thr
1               5
```

<210> SEQ ID NO 6
<211> LENGTH: 10
<212> TYPE: PRT
<213> ORGANISM: murine

<400> SEQUENCE: 6

```
Gly Phe Asp Phe Ser Arg Tyr Trp Met Ser
1               5                   10
```

```
<210> SEQ ID NO 7
<211> LENGTH: 17
<212> TYPE: PRT
<213> ORGANISM: murine

<400> SEQUENCE: 7

Glu Ile Asn Pro Thr Ser Ser Thr Ile Asn Phe Thr Pro Ser Leu Lys
1               5                   10                  15

Asp

<210> SEQ ID NO 8
<211> LENGTH: 12
<212> TYPE: PRT
<213> ORGANISM: murine

<400> SEQUENCE: 8

Gly Asn Tyr Tyr Arg Tyr Gly Asp Ala Met Asp Tyr
1               5                   10

<210> SEQ ID NO 9
<211> LENGTH: 717
<212> TYPE: DNA
<213> ORGANISM: murine

<400> SEQUENCE: 9
atggagacag acacactcct gttatgggta ctgctgctct gggttccagg ttccactggt      60
gacattgcgc tgacacagtc tcctgcttcc ttagctgtat ctctgggaca gagggccacc    120
atctcatgca gggccagcaa aagtgtcagt acatctggct atagttatct gcactggtac    180
caacagaaac aggacagcc acccaaactc ctcatctatc ttgcatccaa cctagaatct    240
ggggtccctg ccaggttcag tggcagtggg tctgggacag acttcaccct caacatccat    300
cctgtggagg aggaggatgc tgcaacctat tactgtcagc acagtaggga gcttccattc    360
acgttcggct cggggacaaa gttggaaata aaacgggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag acagcaaag acagcaccta cagcatgagc    600
agcaccctca cgttgaccaa ggacgagtat gaacgacata cagctatac ctgtgaggcc    660
actcacaaga catcaacttc acccattgtc aagagcttca caggaatga gtgttag       717

<210> SEQ ID NO 10
<211> LENGTH: 1392
<212> TYPE: DNA
<213> ORGANISM: murine

<400> SEQUENCE: 10
atggattttg gctgattttt ttttattgtt gctcttttaa aaggggtcca gtgtgaggtg      60
aagcttctcg agtctggagg tggcctggtg cagcctggag gatccctgaa actctcctgt    120
gcagcctcag gattcgattt cagtagatac tggatgagtt gggtccggca ggctccaggg    180
aaagggctag aatggattgg agagattaat ccaactagca gtacgataaa ctttacgcca    240
tctctaaagg ataaagtctt catctccaga gacaacgcca aaatacgct gtacctgcaa    300
atgagcaaag tgatctga ggacacagcc ctttattact gtgcaagagg gaactactat    360
aggtacggag atgctatgga ctactgggggt caaggaacct cagtcaccgt ctcctcagcc    420
aaaacgacac ccccatctgt ctatccactg gcccctggat ctgctgccca aactaactcc    480
```

-continued

```
atggtgaccc tgggatgcct ggtcaagggc tatttccctg agccagtgac agtgacctgg    540
aactctggat ccctgtccag cggtgtgcac accttcccag ctgtcctgca gtctgacctc    600
tacactctga gcagctcagt gactgtcccc tccagcacct ggcccagcga gaccgtcacc    660
tgcaacgttg cccacccggc cagcagcacc aaggtggaca agaaaattgt gcccagggat    720
tgtggttgta agccttgcat atgtacagtc ccagaagtat catctgtctt catcttcccc    780
ccaaagccca aggatgtgct caccattact ctgactccta aggtcacgtg tgttgtggta    840
gacatcagca aggatgatcc cgaggtccag ttcagctggt ttgtagatga tgtggaggtg    900
cacacagctc agacgcaacc ccgggaggag cagttcaaca gcactttccg ctcagtcagt    960
gaacttccca tcatgcacca ggactggctc aatggcaagg agttcaaatg cagggtcaac   1020
agtgcagctt tccctgcccc catcgagaaa accatctcca aaaccaaagg cagaccgaag   1080
gctccacagg tgtacaccat tccacctccc aaggagcaga tggccaagga taaagtcagt   1140
ctgacctgca tgataacaga cttcttccct gaagacatta ctgtggagtg gcagtggaat   1200
gggcagccag cggagaacta caagaacact cagcccatca tggacacaga tggctcttac   1260
ttcgtctaca gcaagctcaa tgtgcagaag agcaactggg aggcaggaaa tactttcacc   1320
tgctctgtgt tacatgaggg cctgcacaac caccatactg agaagagcct ctcccactct   1380 cctggtaaa tga                                                      1392
```

<210> SEQ ID NO 11
<211> LENGTH: 7
<212> TYPE: PRT
<213> ORGANISM: murine

<400> SEQUENCE: 11

Asp Ile Ala Leu Thr Gln Ser
1               5

<210> SEQ ID NO 12
<211> LENGTH: 7
<212> TYPE: PRT
<213> ORGANISM: murine

<400> SEQUENCE: 12

Glu Val Lys Leu Leu Glu Ser
1               5

<210> SEQ ID NO 13
<211> LENGTH: 238
<212> TYPE: PRT
<213> ORGANISM: murine

<400> SEQUENCE: 13

Met Glu Thr Asp Thr Leu Leu Leu Trp Val Leu Leu Trp Val Pro
1               5                   10                  15

Gly Ser Thr Gly Asp Ile Ala Leu Thr Gln Ser Pro Ala Ser Leu Ala
                20                  25                  30

Val Ser Leu Gly Gln Arg Ala Thr Ile Ser Cys Arg Ala Ser Lys Ser
            35                  40                  45

Val Ser Thr Ser Gly Tyr Ser Tyr Leu His Trp Tyr Gln Gln Lys Pro
        50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

-continued

```
Leu Asn Ile His Pro Val Glu Glu Asp Ala Ala Thr Tyr Tyr Cys
            100                 105                 110

Gln His Ser Arg Glu Leu Pro Phe Thr Phe Gly Ser Gly Thr Lys Leu
        115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys
225                 230                 235

<210> SEQ ID NO 14
<211> LENGTH: 463
<212> TYPE: PRT
<213> ORGANISM: murine

<400> SEQUENCE: 14

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Ser Trp Val Arg Gln Ala Pro Gly Lys Gly Leu Glu
    50                  55                  60

Trp Ile Gly Glu Ile Asn Pro Thr Ser Ser Thr Ile Asn Phe Thr Pro
65                  70                  75                  80

Ser Leu Lys Asp Lys Val Phe Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Gly Asn Tyr Tyr Arg Tyr Gly Asp Ala Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Ala Ala Gln Thr Asp Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Pro Ser Ser Thr Trp Pro Ser Glu Thr Val Thr Cys Asn Val Ala
    210                 215                 220

His Pro Ala Ser Ser Thr Lys Val Asp Lys Lys Ile Val Pro Arg Asp
```

```
                225                 230                 235                 240

Cys Gly Cys Lys Pro Cys Ile Cys Thr Val Pro Glu Val Ser Ser Val
            245                 250                 255

Phe Ile Phe Pro Pro Lys Pro Lys Asp Val Leu Thr Ile Thr Leu Thr
            260                 265                 270

Pro Lys Val Thr Cys Val Val Asp Ile Ser Lys Asp Asp Pro Glu
            275                 280                 285

Val Gln Phe Ser Trp Phe Val Asp Asp Val Glu Val His Thr Ala Gln
            290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                    325                 330                 335

Cys Arg Val Asn Ser Ala Ala Phe Pro Ala Pro Ile Glu Lys Thr Ile
                    340                 345                 350

Ser Lys Thr Lys Gly Arg Pro Lys Ala Pro Gln Val Tyr Thr Ile Pro
            355                 360                 365

Pro Pro Lys Glu Gln Met Ala Lys Asp Lys Val Ser Leu Thr Cys Met
            370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                    405                 410                 415

Asp Gly Ser Tyr Phe Val Tyr Ser Lys Leu Asn Val Gln Lys Ser Asn
                    420                 425                 430

Trp Glu Ala Gly Asn Thr Phe Thr Cys Ser Val Leu His Glu Gly Leu
            435                 440                 445

His Asn His His Thr Glu Lys Ser Leu Ser His Ser Pro Gly Lys
            450                 455                 460

<210> SEQ ID NO 15
<211> LENGTH: 463
<212> TYPE: PRT
<213> ORGANISM: murine

<400> SEQUENCE: 15

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
            35                  40                  45

Arg Tyr Trp Met Ser Trp Val Arg Gln Ala Pro Gly Lys Gly Leu Glu
    50                  55                  60

Trp Ile Gly Glu Ile Asn Pro Thr Ser Ser Thr Ile Asn Phe Thr Pro
65                  70                  75                  80

Ser Leu Lys Asp Lys Val Phe Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Gly Asn Tyr Arg Tyr Gly Asp Ala Met Asp Tyr
            115                 120                 125

Trp Gly Gln Gly Thr Ser Val Thr Val Ser Ser Ala Lys Thr Thr Pro
            130                 135                 140
```

```
Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
            165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
            195                 200                 205

Val Pro Ser Ser Thr Trp Pro Ser Glu Thr Val Thr Cys Asn Val Ala
            210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
                260                 265                 270

Pro Lys Val Thr Cys Val Val Val Asp Ile Ser Lys Asp Asp Pro Glu
            275                 280                 285

Val Gln Phe Ser Trp Phe Val Asp Asp Val Glu Val His Thr Ala Gln
290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
                340                 345                 350

Ser Lys Thr Lys Gly Arg Pro Lys Ala Pro Gln Val Tyr Thr Ile Pro
            355                 360                 365

Pro Pro Lys Glu Gln Met Ala Lys Asp Lys Val Ser Leu Thr Cys Met
370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
            405                 410                 415

Asp Gly Ser Tyr Phe Val Tyr Ser Lys Leu Asn Val Gln Lys Ser Asn
            420                 425                 430

Trp Glu Ala Gly Asn Thr Phe Thr Cys Ser Val Leu His Glu Gly Leu
        435                 440                 445

His Asn His His Thr Glu Lys Ser Leu Ser His Ser Pro Gly Lys
450                 455                 460
```

UNITED STATES PATENT AND TRADEMARK OFFICE
CERTIFICATE OF CORRECTION

PATENT NO. : 11,241,512 B2
APPLICATION NO. : 16/456614
DATED : February 8, 2022
INVENTOR(S) : Kaushik Dave and Shubh Sharma It is certified that error appears in the above-identified patent and that said Letters Patent is hereby corrected as shown below:

In the Claims

Column 33, Line 67, Claim 2:
Delete "from $^{131}$I, $^{90}$Y, $^{177}$Lu, $^{186}$Re, or $^{188}$e", and insert --from $^{131}$I, $^{90}$Y, $^{177}$Lu, $^{186}$Re, or $^{188}$Re--, therefor.

Column 35, Line 14, Claim 8:
Delete "from $^{131}$I, $^{90}$Y, $^{177}$Lu, $^{186}$Re, or $^{188}$e", and insert --from $^{131}$I, $^{90}$Y, $^{177}$Lu, $^{186}$Re, or $^{188}$Re--, therefor.

Signed and Sealed this
Tenth Day of May, 2022

Katherine Kelly Vidal
*Director of the United States Patent and Trademark Office*